(12) United States Patent
Kelly et al.

(10) Patent No.: US 10,925,887 B2
(45) Date of Patent: Feb. 23, 2021

(54) STEROID SAPONINS WITH ANTI-CANCER ACTIVITY

(71) Applicant: Oncology Research International Limited, Perth (AU)

(72) Inventors: Peter Kelly, Lower Hutt (NZ); Philip Andrew Marshall, Tennyson (AU)

( * ) Notice: Subject to any disclaimer, the term of this patent is extended or adjusted under 35 U.S.C. 154(b) by 0 days.

(21) Appl. No.: 16/484,949

(22) PCT Filed: Feb. 9, 2018

(86) PCT No.: PCT/AU2018/050099
§ 371 (c)(1),
(2) Date: Aug. 9, 2019

(87) PCT Pub. No.: WO2018/145162
PCT Pub. Date: Aug. 16, 2018

(65) Prior Publication Data
US 2019/0358252 A1    Nov. 28, 2019

(30) Foreign Application Priority Data

Feb. 10, 2017    (AU) .............................. 2017900427

(51) Int. Cl.
| C07J 71/00 | (2006.01) |
| C07J 19/00 | (2006.01) |
| A61K 31/7048 | (2006.01) |
| A61P 35/00 | (2006.01) |

(52) U.S. Cl.
CPC .......... *A61K 31/7048* (2013.01); *A61P 35/00* (2018.01); *C07J 19/00* (2013.01); *C07J 71/00* (2013.01); *C07J 71/0005* (2013.01)

(58) Field of Classification Search
None
See application file for complete search history.

(56) References Cited

FOREIGN PATENT DOCUMENTS

| CN | 1322729 | 11/2001 |
| CN | 104098646 | 10/2014 |
| WO | WO 2008/014563 | 2/2008 |
| WO | WO 2008/014564 | 2/2008 |
| WO | WO 2013/173862 | 11/2013 |

OTHER PUBLICATIONS

Hernandez et al., Bioorganic and Medicinal Chemistry, 2008, 16(4), pp. 2063-2076. (Year: 2008).*
Chu et al., "Profiling the Ginsenosides of Three Ginseng Products by Lc-Q-Tof/Ms," *Journal of Food Science*, vol. 78, No. 5, pp. C653-C659, 2013.
Li et al., "Synthesis, cytotoxicity, and hemolytic activity of 6'-O-substituted dioscin derivatives," *Carbohydrate Research*, vol. 342, pp. 2705-2715, 2007.
Ali et al., "Two Spirostan Steroid Glycoside Fatty Esters from *Dioscorea cayenensis*," *Natural Product Communications*, vol. 8, No. 3, pp. 323-326, 2013.
Hernandez et al., "Synthesis of novel spirostanic saponins and their cytotoxic activity," *Bioorganic & Medicinal Chemistry*, vol. 16, pp. 2063-2076, 2008.
Matsuo et al., "New Steroidal Glycosides from Rhizomes of *Clintonia udensis*," *Bioscience, Biotechnology, and Biochemistry*, vol. 72, No. 7, pp. 1714-1721, 2008.
Sun et al., "Diosgenin Glucuronides from *Solanum lyratum* and their Cytotoxicity against Tumor Cell Lines," *Z. Naturforsch.* (*Journal of Biosciences*), vol. 61, No. 34, pp. 171-176, 2006.
Supplementary European Search Report from corresponding EP App. No. 18751532, dated Dec. 4, 2020 (14 pages).
Wang et al., "Exploration of the correlation between the structure, hemolytic activity, and cytotoxicity of steroid saponins," *Bioorganic & Medicinal Chemistry*, vol. 15, pp. 2528-2532, 2007.
Wu et al., "New Steroidal Saponins and Sterol Glycosides and *Paris polyphylla* var. *yunnanensis*," *Planta Medica*, vol. 78, No. 15, pp. 1667-1675, 2012.
Yu et al., "Lipase-catalyzed regioselective acylation of diosgenyl saponins," *Tetrahedron Letters*, vol. 42, pp. 5513-5516, 2001.

* cited by examiner

*Primary Examiner* — Traviss C McIntosh, III
(74) *Attorney, Agent, or Firm* — Klarquist Sparkman, LLP

(57) ABSTRACT

The present invention relates to a new class of steroid saponins that have interesting biological activity. In particular the present invention relates to a class of steroid saponins in which the sugar moiety has been selectively functionalised to introduce a moiety that contains either, (i) a hydrogen ion donor, (ii) a hydrogen ion acceptor or (iii) a combination thereof. These new, water-soluble compounds are found to not only have potent anti-cancer properties per se but also have the ability to promote the immune response in a subject and can thus act as adjuvants for T-cell activation in cancer therapy.

22 Claims, 1 Drawing Sheet

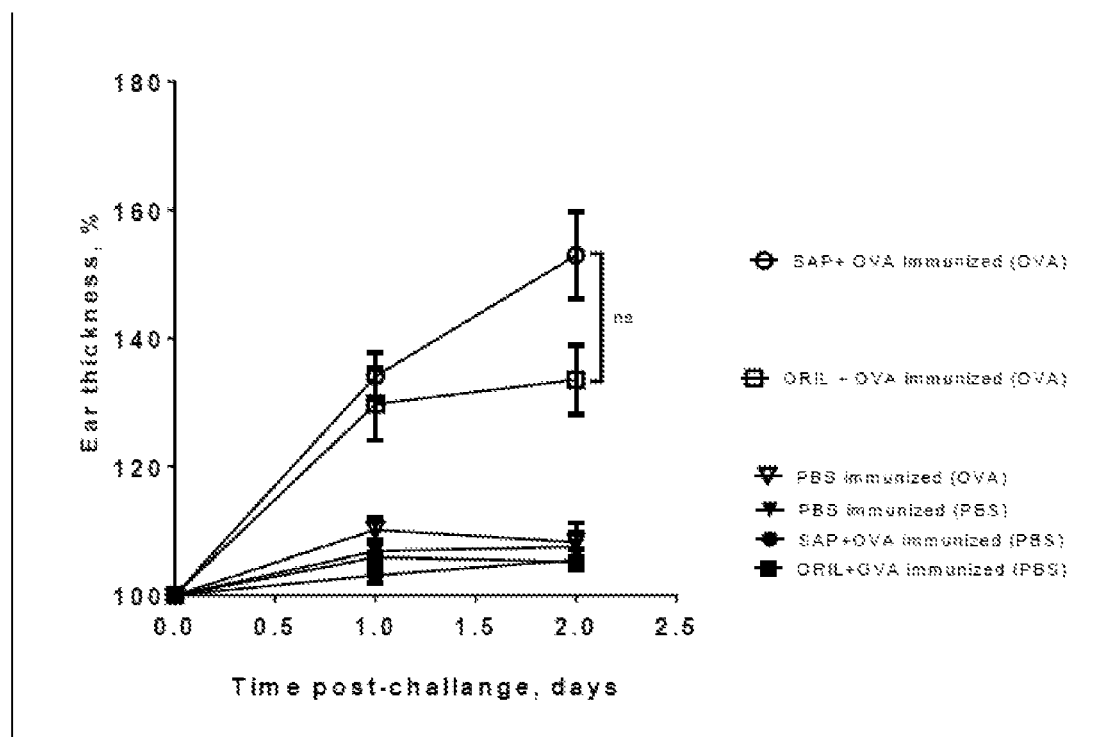

STEROID SAPONINS WITH ANTI-CANCER ACTIVITY

CROSS REFERENCE TO RELATED APPLICATIONS

This is the § 371 U.S. National Stage of International Application No. PCT/AU2018/050099, filed Feb. 9, 2018, which was published in English under PCT Article 21(2), which claims the benefit of AU Application No. 2017900427, filed Feb. 10, 2017, which is incorporated herein by reference in its entirety.

TECHNICAL FIELD

The present invention relates to a new class of steroid saponins that have interesting biological activity. In particular the present invention relates to a class of steroid saponins in which the sugar moiety has been selectively functionalised to introduce a moiety that contains either, (i) a hydrogen ion donor, (ii) a hydrogen ion acceptor or (iii) a combination thereof. These new, water-soluble compounds are found to not only have potent anti-cancer properties per se but also have the ability to potentiate the activity of other anti-cancer agents. For example the compounds have the ability to promote the immune response in a subject and can thus act as adjuvants for T-cell activation in cancer therapy.

BACKGROUND OF INVENTION

Cancer is a leading cause of death worldwide, with an estimated 14.1 cases diagnosed and 8.2 million people dying from cancer in 2012 alone, rising to a predicted 13 million deaths by 2030, according to the World Health Organisation. These figures are expected to rise as life expectancy increases, and as lifestyle, diet and/or environmental factors change over time increasing risk factors for the condition.

Notwithstanding that there have been great improvements in the diagnosis and treatment of cancer, many people still die from cancer each year, and their deaths are typically due to metastases and cancers that are resistant to conventional therapies. Current methods for treatment of advanced and/or metastatic malignancies previously treated with chemotherapy (i.e. chemotherapy-refractory cancers) are inadequate from an efficacy and safety standpoint. Accordingly there is a continued need to develop alternative pharmaceutical agents that may be used in the treatment of cancer.

One potential group of candidates in this area are the steroid saponins. Steroid saponins are a class of secondary metabolites derived from various plant and marine species and are of particular interest as novel active agents due to their remarkable bioactivity. Some saponins have been shown to bind and cross cell membranes, others have been utilised as surfactants, still others have been used as adjuvants in vaccines. Saponins have also been utilised in Chinese medicine and as such, have been promoted as dietary supplements. Furthermore, some steroid saponins are known to enhance the activity of a number of chemotherapeutic and anti-cancer agents, ultimately inhibiting growth of cancerous cells. Other steroid saponins have demonstrated an ability to inhibit angiogenesis in a number of in vivo and ex vivo model systems. Accordingly, steroid saponins provide a class of interesting molecules with diverse biological activity.

Indeed in commonly owned International applications PCT/AU2007/001091 and PCT/AU2007/001092 the present applicants have described advantageous therapeutic applications, compositions and uses of some steroid saponins that occur in nature.

Of the previously reported steroid saponins the compound diosgenyl α-L-rhamnopyranosyl-(1→2)-β-D-glucopyranoside (Compound A) is a known natural compound that occurs in trace amounts in a number of rare plant species. The compound shows significant promise as a pharmaceutically active agent for the treatment of a number of medical conditions and clinical development of this compound is underway based on the activity profiles demonstrated by the compound.

Compound A

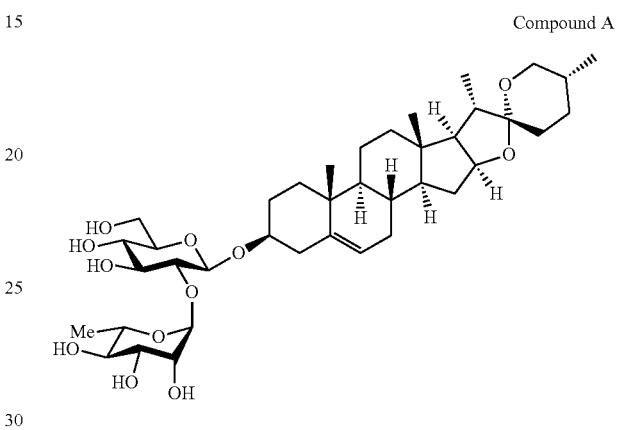

Notwithstanding the significant promise shown by this compound as a therapeutic agent there still remains a great need for new compounds and therapies to treat all manner of pathogenic, deficiency, hereditary and physiological diseases. In particular, with rising life expectancies, there has been a significant rise in the incidence of non-infectious, age-related diseases, such as cancer as discussed above.

Unfortunately whilst a number of steroid saponins, including Compound A have shown significant promise as active pharmaceutical ingredients they have not been readily used. This may be due to the fact that in general they are sparingly soluble or insoluble in water and under physiological conditions, even in combination with pharmaceutically acceptable carriers or excipients and as such are very difficult to formulate and administer. As would be appreciated by a skilled worker in the field the water solubility of a potential active pharmaceutical agent (or drug) is a significant physiochemical property in formulation. Upon oral administration the solubility and permeability properties of a drug have the most impact on the ultimate absorption of the drug into the systemic circulation from the gastrointestinal tract, i.e. the drug's bioavailablity, and therefore its therapeutic effectiveness, and where systemic absorption is necessary. Accordingly, in circumstances where the native or inherent solubility of the active agent is low it is critical to be able to formulate it in such a way to make it bioavailable at an acceptable level.

Accordingly it would be desirable to identify alternative water-soluble steroid saponins that may find applications in the treatment of diseases such as cancer. As a result of their studies the present applicants have identified and designed a new family of steroid saponins that demonstrate improved properties in comparison to the known naturally occurring steroid saponins.

SUMMARY OF INVENTION

The present invention provides a compound of the formula (I)

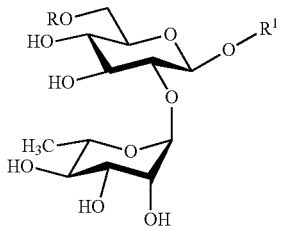

Formula I wherein

R is a moiety containing either (1) at least one a hydrogen ion donor, (2) at least one hydrogen ion acceptor or (3) a combination thereof; and $R^1$ is a group of Formula E, F or G, as defined hereinbelow;

or a pharmaceutically acceptable salt thereof.

The applicants have found that in many instances compounds of this type have increased potency in comparison with the known compounds and may also demonstrate improved safety profiles. In the compounds of the invention R is not H.

As discussed above the present applicants have found that the new steroid saponins may be used in the treatment of cancer. Accordingly the present invention also provides a method of treatment of cancer in a subject the method comprising administration of a therapeutically effective amount of a compound of the invention to a subject in need thereof.

In addition to having anti-cancer activity themselves the applicants have also found that the compounds of the invention have the potential to potentiate or promote the activity of other anti-cancer therapies. Accordingly in yet an even further aspect the present invention provides a method of promoting the activity of an anti-cancer therapy in a subject the method comprising administration of an effective amount of a compound of the invention to a subject in need thereof.

The applicants have also found that the compounds of the invention have the ability to act as adjuvants in that they demonstrate the ability to activate the immune response in a subject. Accordingly in yet a further aspect the present invention provides a method of promoting an immune response in a subject, the method comprising administration of an effective amount of a compound of the invention to a subject in need thereof.

In yet an even further aspect the invention provides the use of the compound of the invention as an adjuvant.

BRIEF DESCRIPTION OF DRAWINGS

FIG. 1 shows the results of a study into the ability of one of the compounds of the invention to act as an adjuvant.

DETAILED DESCRIPTION

Definitions

In this specification a number of terms are used which are well known to a skilled addressee. Nevertheless for the purposes of clarity a number of terms will be defined.

As used herein, the term "treating" in relation to cancer means to inhibit, reduce, diminish, arrest, or stabilize a tumour or other feature associated with cancer, or one or more symptoms thereof.

Thus "treating" could result in regression or eradication of the tumour or other feature associated with cancer; or it could result in maintenance of the size of the tumour so that it does not increase, or that it increases by a lesser amount compared with a standard therapy.

The term "subject in need thereof" means a human or an animal that has or is diagnosed with cancer, or is predisposed or susceptible to cancer, or is at risk of developing cancer.

The term "therapeutically effective amount" or "effective amount" means an amount sufficient to effect beneficial or desired clinical results, such as to palliate, ameliorate, stabilize, reverse, slow or delay the progression of the cancer. An effective amount can be administered in one or more administrations.

The term "pharmaceutically acceptable salts" refers to salts that retain the desired biological activity of the above-identified compounds, and include pharmaceutically acceptable acid addition salts and base addition salts. Suitable pharmaceutically acceptable acid addition salts of compounds of Formula (I) may be prepared from an inorganic acid or from an organic acid. Examples of such inorganic acids are hydrochloric, sulfuric, and phosphoric acid. Appropriate organic acids may be selected from aliphatic, cycloaliphatic, aromatic, heterocyclic carboxylic and sulfonic classes of organic acids, examples of which are formic, acetic, propanoic, succinic, glycolic, gluconic, lactic, malic, tartaric, citric, fumaric, maleic, alkyl sulfonic, arylsulfonic. Additional information on pharmaceutically acceptable salts can be found in P. H. Stahl and C. G. Wermuth Handbook of Pharmaceutical Salts, Properties, Selection, and Use, $2^{nd}$ Revised Edition, Wiley-VCH 2011. In the case of agents that are solids, it is understood by those skilled in the art that the inventive compounds, agents and salts may exist in different crystalline or polymorphic forms, all of which are intended to be within the scope of the present invention and specified formulae.

As used herein the term "hydrogen ion donor" means a group that under suitable conditions can ionise to release a $H^+$ ion and to produce a negatively charged species. Examples of groups of this type include inorganic acids, sulfonic acids, carboxylic acids, anionic amino acids, hydroxyl acids, fatty acids for insoluble salts, that is denoted by $-CO_2H$, $-SO_3H$ and $-PO_3H_2$.

As used herein the term "hydrogen ion acceptor" means a group that under suitable conditions can react with $H^+$ ion to form a positively charged species. Examples of groups of this type include organic amines, cationic amines and bases for insoluble salts.

The term "saponin" as used throughout the specification is to be understood to mean a glycoside including a saccharide (sugar) attached to the aglycone, generally through the C-3 position of the aglycone.

The term "steroid saponin" as used throughout the specification is to be understood to mean a glycoside including one or more saccharide units (including one or more monosaccharide, disaccharide or polysaccharide units) attached to an aglycone and which does not contain a nitrogen atom.

In this regard, it will be understood that the term "steroid saponin" includes within its scope any salts or any other derivatives of the compounds that are functionally equivalent, in particular with respect of therapeutic active agents.

As such, they may be pharmaceutically acceptable salts. Furthermore, they may be naturally-occurring or synthetic steroid saponins.

The term 'adjuvant' as used throughout the specification refers to a compound or material that either (i) enhances or promotes an immune response to an agent in a subject or (ii) facilitates or modifies the action of a principal agent in a subject.

As stated above the present invention provides a compound of the formula (I)

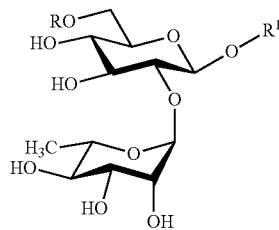

Formula I wherein

R is a moiety containing either (1) at least one a hydrogen ion donor, (2) at least one hydrogen ion acceptor or (3) a combination thereof; and $R^1$ is a group of Formula E, F or G:

Formula E wherein $R^{11}$, $R^{12}$, $R^{14}$, $R^{16}$, $R^{17}$, $R^{21}$, $R^{22}$, $R^{24}$, $R^{25}$ and $R^{27}$ are independently H, OH, =O, pharmacologically acceptable ester groups or pharmacologically acceptable ether groups;

$R^{15}$ is H when C-5,C-6 is a single bond, and nothing when C-5,C-6 is a double bond;

A is either O concurrently with B being $CH_2$, or B is O concurrently with A being $CH_2$;

$R^{37A}$ is H concurrently with $R^{37B}$ being $CH_3$, or $R^{37A}$ is $CH_3$ concurrently with $R^{37B}$ being H;

or a pharmaceutically acceptable salt thereof;

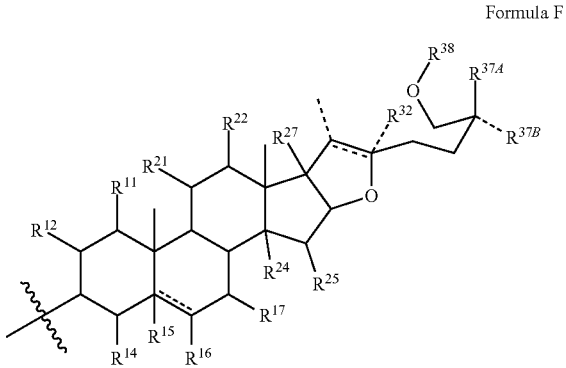

Formula F wherein $R^{11}$, $R^{12}$, $R^{14}$, $R^{16}$, $R^{17}$, $R^{21}$, $R^{22}$, $R^{24}$, $R^{25}$ and $R^{27}$ are independently H, OH, =O, pharmacologically acceptable ester groups or pharmacologically acceptable ether groups;

$R^{15}$ is H when C-5, C-6 is a single bond, and nothing when C-5, C-6 is a double bond;

$R^{32}$ is either a hydroxyl or an alkoxyl group when C-20, C-22 is a single bond, or nothing when C-20, C-22 is a double bond;

$R^{37A}$ is H concurrently with $R^{37B}$ being $CH_3$, or $R^{37A}$ is $CH_3$ concurrently with $R^{37B}$ being H;

$R^{38}$ is H or a saccharide; or a pharmaceutically acceptable salt thereof;

or a pharmaceutically acceptable salt thereof;

Formula G wherein $R^{11}$, $R^{12}$, $R^{14}$, $R^{16}$, $R^{17}$, $R^{21}$, $R^{22}$, $R^{24}$, $R^{25}$ and $R^{27}$ are each independently H, OH, =O, pharmacologically acceptable ester groups or pharmacologically acceptable ether groups;

$R^{15}$ is H when C-5, C-6 is a single bond, and nothing when C-5, C-6 is a double bond;

$R^{32}$ and $R^{39}$ are each independently H, OH, =O, pharmacologically acceptable ester groups or pharmacologically acceptable ether groups;

$R^{37A}$ is H concurrently with $R^{37B}$ being $CH_3$, or $R^{37A}$ is $CH_3$ concurrently with $R^{37B}$ being H;

$R^{38}$ is H or a saccharide; or a pharmaceutically acceptable salt thereof;

or a pharmaceutically acceptable salt thereof.

In one embodiment the group R¹ is chosen such that the compound has the formula II as shown below:

Formula II

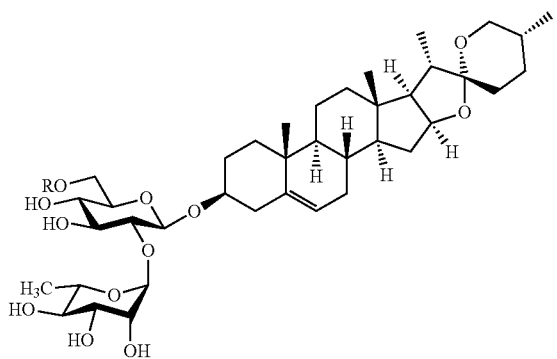

wherein R is as defined above or a pharmaceutically acceptable salt thereof.

As discussed above in the compounds of the invention the group R is a moiety containing either (1) at least one a hydrogen ion donor, (2) at least one hydrogen ion acceptor or (3) a combination thereof. Without wishing to be bound by theory it is thought by the applicant that incorporation of a group of this type at this position leads to improved pharmaceutical-technological properties of the molecule leading to an improved pharmacokinetic profile. In particular, without wishing to be bound by theory, incorporation of a group of this type may lead to improvements in the absorption, distribution, metabolism, or excretion of the compound following its administration.

In essence the R group can be any of a large number potential moieties as long as it can be viably attached to the oxygen atom and contains either (1) at least one hydrogen ion donor, (2) at least one hydrogen ion acceptor or (3) a combination thereof. The group may be a simple organic substituent such as an alkyl or aryl group containing a suitable substituent or it may be a more complex substituent such as an amino acid group. As stated above R is not H.

In one embodiment the R group is a moiety containing at least one hydrogen ion donor. As discussed above a hydrogen ion donor is a group that under suitable conditions can ionise to form a negatively charged species and a hydrogen ion (H⁺). In essence any "acidic group" or moiety will in general have this ability. In one embodiment the R group is a $C_1$-$C_6$ alkyl group containing a hydrogen ion donor substituent. Examples of suitable hydrogen ion donors include —$CO_2H$, —$SO_3H$ and —$PO_3H_2$.

In one embodiment R includes a hydrogen ion donor of the formula —$CO_2H$. In one embodiment R includes a hydrogen ion donor of the formula —$SO_3H$. In one embodiment R includes a hydrogen ion donor of the formula and —$PO_3H_2$.

In certain embodiments the entirety of the R moiety may be a hydrogen ion donor. In one embodiment R is —$SO_3H$. In one embodiment R is —$PO_3H_2$.

In one embodiment the group R is a moiety containing at least one hydrogen ion acceptor. As discussed above term "hydrogen ion acceptor" means a group that under suitable conditions can react with H⁺ion to form a positively charged species.

There are a large range of hydrogen ion acceptors that would be well understood by a skilled worker in the field. In one embodiment the hydrogen ion acceptor is a group of the formula —$NH_2$. In one embodiment R is a group of the formula $(CH_3)_2CHCH(NH_2)C(=O)$—.

In one embodiment of the invention the compound is a compound of the formula (III):

Formula (III)

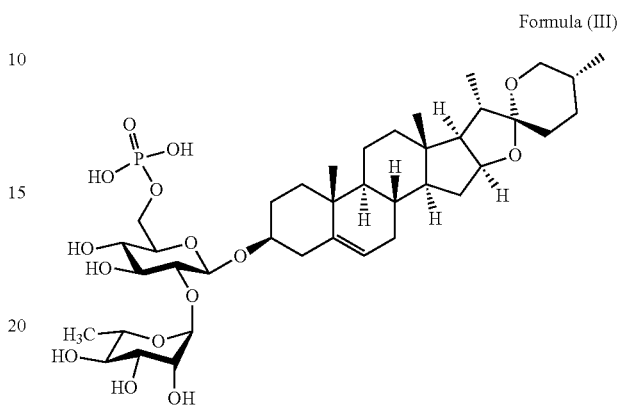

or a pharmaceutically acceptable salt thereof.

In one embodiment of the invention the compound is a compound of the formula (IV):

Formula (IV)

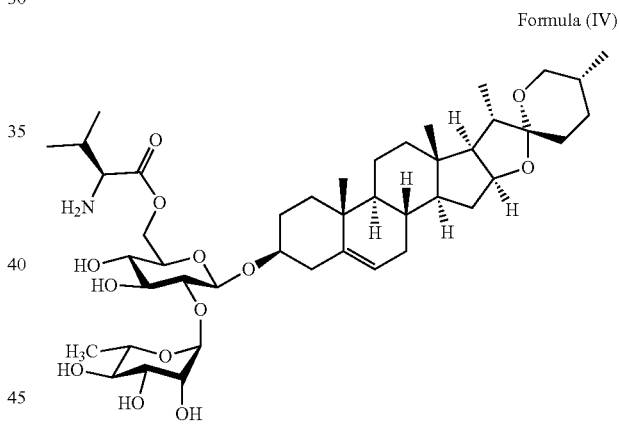

or a pharmaceutically acceptable salt thereof.

In one embodiment the compound has the formula:

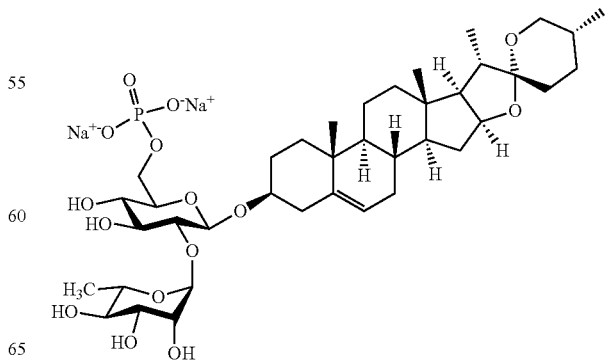

In one embodiment the compound has the formula:

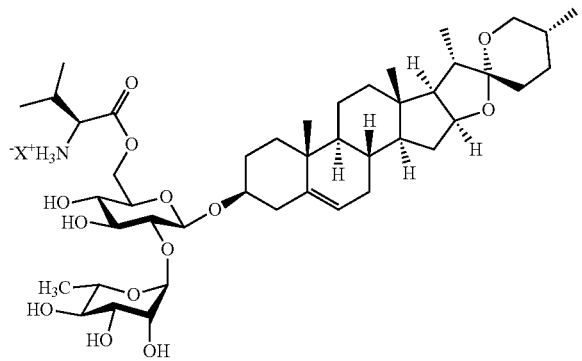

wherein X is HO$_2$CCHCHCO$_2$—.

As stated above the compounds may be in the form of a pharmaceutically acceptable salt. In circumstances where the R group contains a hydrogen ion donor the pharmaceutically acceptable salt is derived from a base. Examples of suitable salts include the sodium, potassium, calcium, magnesium and zinc salt. In one embodiment the salt is the potassium salt. In one embodiment the salt is the sodium salt. In one embodiment the salt is the calcium salt. In one embodiment the salt is the magnesium salt. In one embodiment the salt is the zinc salt.

In circumstances where the R group contains a hydrogen ion acceptor the salt is typically derived from an acid. Examples of suitable acid addition salts include the hydrobromide, hydrochloride sulfate, nitrate, phosphate mesylate, esylate, isethionate, tosylate, napsylate, besylate, acetate, propionate, benzoate, salicylate, fumurate, glutamate, aspartate, lacatate, succinate, tartrate, glycolate, hexanoate, octanoate, decanoate, oleate, stearate pamoatecitrate, and the maleate salt. In one embodiment the salt is the citrate salt.

In one embodiment the salt is the maleate salt. In one embodiment the salt is the hydrochloride salt.

The compounds of the present invention have been found to have beneficial application in the treatment of certain cancers. Accordingly the present invention also provides a method of treatment of cancer the method comprising administration of a therapeutically effective amount of a compound of the invention to a subject in need thereof.

The compounds may be used in the treatment of a wide range of cancer types. wherein the cancer is selected from the group consisting carcinoma, bladder cancer, bone cancer, brain tumours, breast cancer, cervical cancer, colorectal cancer including cancer of the colon, rectum, anus, and appendix, cancer of the oesophagus, Hodgkin's disease, kidney cancer, cancer of the larynx, leukaemia, liver cancer, lung cancer, lymphoma, melanoma, moles and dysplastic nevi, multiple myeloma, muscular cancer, non-Hodgkin's lymphoma, oral cancer, ovarian cancer, cancer of the pancreas, prostate cancer, sarcoma, skin cancer, stomach cancer, testicular cancer, teratoma, thyroid cancer, and cancer of the uterus.

Administration of compounds within Formula (I) to humans can be by any of the accepted modes for enteral administration such as oral or rectal, or by parenteral administration such as subcutaneous, intramuscular, intravenous and intradermal routes, or by inhaled compound delivery. Injection can be bolus or via constant or intermittent infusion. Examples of routes include topical administration, enteral administration (i.e. via the intestines, such as oral, gastric tube, or rectally) or parenteral administration (such as injections, e.g., intravenous, intramuscular, subcutaneous or intraperitoneal injection).

The active compound is typically included in a pharmaceutically acceptable carrier or diluent and in an amount sufficient to deliver to the patient a therapeutically effective dose.

In using the compounds of the invention they can be administered in any form or mode which makes the compound bioavailable. One skilled in the art of preparing formulations can readily select the proper form and mode of administration depending upon the particular characteristics of the compound selected, the condition to be treated, the stage of the condition to be treated and other relevant circumstances. We refer the reader to P. H. Stahl and C. G. Wermuth (Eds), Handbook of Pharmaceutical Salts, Properties, Selection, and Use, 2$^{nd}$ Revised Edition, Wiley-VCH (2011) for further information.

The compounds of the present invention can be administered alone or in the form of a pharmaceutical composition in combination with a pharmaceutically acceptable carrier, diluent or excipient. The compounds of the invention, while effective themselves, are typically formulated and administered in the form of their pharmaceutically acceptable salts as these forms are typically more stable, more easily crystallised and have increased water-solubility.

The compounds are, however, typically used in the form of pharmaceutical compositions which are formulated depending on the desired mode of administration. As such in some embodiments the present invention provides a pharmaceutical composition including a compound of Formula (I) and a pharmaceutically acceptable carrier, diluent or excipient. The compositions are prepared in manners well known in the art.

The invention in other embodiments provides a pharmaceutical pack or kit comprising one or more containers filled with one or more of the ingredients of the pharmaceutical compositions of the invention. In such a pack or kit can be found a container having a unit dosage of the agent(s). The kits can include a composition comprising an effective agent either as concentrates (including lyophilized compositions), which can be diluted further prior to use or they can be provided at the concentration of use, where the vials may include one or more dosages. Conveniently, in the kits, single dosages can be provided in sterile vials so that the physician can employ the vials directly, where the vials will have the desired amount and concentration of agent(s). Associated with such container(s) can be various written materials such as instructions for use, or a notice in the form prescribed by a governmental agency regulating the manufacture, use or sale of pharmaceuticals or biological products, which notice reflects approval by the agency of manufacture, use or sale for human administration.

The compounds of the invention may be used or administered in combination with one or more additional drug(s) for the treatment of the disorder/diseases mentioned. The components can be administered in the same formulation or in separate formulations. If administered in separate formulations the compounds of the invention may be administered sequentially or simultaneously with the other drug(s).

Indeed in one embodiment the method of the present invention comprises administration of a second anti-cancer agent. A wide range of second anti-cancer agents may be used in combination with the compounds of the invention. Examples of suitable second anti cancer agents include second anti-cancer agent is selected from one or more of a chemotherapeutic agent, an alkylating agent including BCNU (carmustine), bisulfan, CCNU (lomustine), chlorambucil, cisplatin, melphan, mitomycin C, and thio-tepa; an antimitotic agent including taxol (paclitaxel), docetaxel, vinblastine sulphate, and vincristine sulphate; a topoisomerase inhibitor including doxorubicin, daunorubicin, m-AMSA (amsacrine), mitoxantrone, and VP-16 (etoposide); a RNA/DNA antimetabolite including 5-fluorouracil and methotrexate; a DNA antimetabolite including Ara-C (cytarabine), hydroxyurea (hydroxycarbamide), and thioguanine (tioguanine); a cellular process targeting agent; imatinib mesylate; trastuzumab; and gefitinib, anti (programmed cell death 1 receptor) PD-1 therapy; prembrozilab and nivomulab.

Indeed without wishing to be bound by theory it is believed that the compounds of the present invention have the ability to promote the activity of an anti-cancer therapy in a subject. In yet an even further embodiment the present invention provides a method of promoting the activity of an anti-cancer therapy in a subject the method comprising administration of an effective amount of a compound of the invention to a subject in need thereof. Indeed the applicants have found that the compounds have adjuvant activity in that they drive T-cell activation and that has the net effect of promoting the activity of an anti-cancer therapy.

As stated above the compounds of the invention may be used as adjuvants whereby they promote an immune response in a subject to other active agent or agents. When used in this way the compounds of the invention may be administered in combination simultaneously with the other agent or agents, or sequentially with the other agent or agents (in any order).

In addition to being able to be administered in combination with one or more additional drugs, the compounds of the invention may therefore be used in a combination therapy. When this is done the compounds are typically administered in combination with each other. Thus one or more of the compounds of the invention may be administered either simultaneously (as a combined preparation) or sequentially in order to achieve a desired effect. This is especially desirable where the therapeutic profile of each compound is different such that the combined effect of the two drugs provides an improved therapeutic result.

Pharmaceutical compositions of this invention for parenteral injection comprise pharmaceutically acceptable sterile aqueous or non-aqueous solutions, dispersions, suspensions or emulsions as well as sterile powders for reconstitution into sterile injectable solutions or dispersions just prior to use. Examples of suitable aqueous and non-aqueous carriers, diluents, solvents or vehicles include water, ethanol, polyols (such as glycerol, propylene glycol, polyethylene glycol, and the like), and suitable mixtures thereof, vegetable oils (such as olive oil), and injectable organic esters such as ethyl oleate. Proper fluidity can be maintained, for example, by the use of coating materials such as lecithin, by the maintenance of the required particle size in the case of dispersions, and by the use of surfactants.

Examples of compositions suitable for topical administration include creams, lotions, eye drops, ear drops, sprays, inhalants, or as an embedded preparation or as a transmucosal preparation through nasal cavity, rectum, uterus, vagina, lung, etc. and the like. Examples of compositions suitable for enteral administration include tablets, pills, granules, powders, capsules, liquid formulations, elixirs, suspensions, wafers, emulsions, syrups, suppositories, and the like. Examples of compositions suitable for parenteral administration include injections or depot preparations such as an implantable pellet, and the like.

Compositions for parenteral injection comprise pharmaceutically acceptable sterile aqueous or non-aqueous solutions, dispersions, suspensions or emulsions as well as sterile powders for reconstitution into sterile injectable solutions or dispersions just prior to use. Examples of suitable aqueous and non-aqueous carriers, diluents, solvents or vehicles include water, ethanol, polyols (such as glycerol, propylene glycol, polyethylene glycol, and the like), and suitable mixtures thereof, vegetable oils (such as olive oil), and injectable organic esters such as ethyl oleate. Proper fluidity can be maintained, for example, by the use of coating materials such as lecithin, by the maintenance of the required particle size in the case of dispersions, and by the use of surfactants.

These compositions may also contain excipients such as preservative, wetting agents, emulsifying agents, buffering agents, pH controller, isotonic agent and dispersing agents. Prevention of the action of micro-organisms may be ensured by the inclusion of various antibacterial and antifungal agents, for example, paraben, chlorobutanol, phenol sorbic acid, and the like. It may also be desirable to include isotonic agents such as sugars, sodium chloride, and the like. These excipients are well known to those skilled in the art.

Examples of suitable preservatives are benzoic acid esters of para-hydroxybenzoic acid, 20 phenols, phenylethyl alcohol or benzyl alcohol. Examples of suitable buffers are sodium phosphate salts, citric acid, tartaric acid and the like. Examples of suitable stabilisers are antioxidants such as alpha-tocopherol acetate, alpha-thioglycerin, sodium metabisulphite, ascorbic acid, acetylcysteine, 8-hydroxyquinoline, and chelating agents such as disodium edetate. Examples of suitable viscosity enhancing agents, suspending, 25 solubilizing or dispersing agents are substituted cellulose ethers, substituted cellulose esters, polyvinyl alcohol, polyvinylpyrrolidone, polyethylene glycols, carbomer, polyoxypropylene glycols, sorbitan monooleate, sorbitan sesquioleate, polyoxyethylene hydrogenated castor oil 60.

Examples of suitable pH controllers include hydrochloric acid, sodium hydroxide, buffers and the like. Examples of suitable isotonic agents are glucose, D-sorbitol or D-mannitol, sodium chloride.

Prolonged absorption of the injectable pharmaceutical form may be brought about by the inclusion of agents that delay absorption such as aluminium monostearate and gelatin. These agents are well known to those skilled in the art.

If desired, and for more effective distribution, the compounds can be incorporated into slow release or targeted delivery systems such as polymer matrices, liposomes, and microspheres.

The injectable formulations can be sterilized, for example, by heat, irradiation or by filtration through a bacterial-retaining filter, or by incorporating sterilizing agents in the form of sterile solid compositions that can be dissolved or dispersed in sterile water or other sterile injectable medium just prior to use.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like.

The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes.

The active compounds can also be in microencapsulated form, if appropriate, with one or more of the above-mentioned excipients.

Liquid dosage forms for oral administration include pharmaceutically acceptable emulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethyl formamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavouring, and perfuming agents.

Suspensions, in addition to the active compounds, may contain suspending agents as, for example, ethoxylated isostearyl alcohols, polyoxyethylene sorbitol and sorbitan esters, microcrystalline cellulose, aluminium metahydroxide, bentonite, agar-agar, and tragacanth, and mixtures thereof.

Compositions for rectal or vaginal administration are preferably suppositories which can be prepared by mixing the compounds of this invention with suitable non-irritating excipients or carriers such as cocoa butter, polyethylene glycol or a suppository wax which are solid at room temperature but liquid at body temperature and therefore melt in the rectum or vaginal cavity and release the active compound.

Dosage forms for topical administration of a compound of this invention include powders, patches, sprays, ointments and inhalants. The active compound is mixed under sterile conditions with a pharmaceutically acceptable carrier and any needed preservatives, buffers, or propellants which may be required.

Suitable compositions can be prepared by methods commonly employed using conventional, organic or inorganic additives, such as an excipient. Such excipients may be selected from fillers or diluents, binders, disintegrants, lubricants, flavouring agents, preservatives, stabilizers, suspending agents, dispersing agents, surfactants, antioxidants or solubilizers.

Examples of fillers or diluents include sucrose, starch, mannitol, sorbitol, lactose, glucose, cellulose, talc, calcium phosphate or calcium carbonate, and the like. Examples of binders include cellulose, carboxymethylcellulose, methylcellulose, hydroxymethylcellulose, hydroxy-propylmethylcellulose, polypropylpyrrolidone, polyvinylpyrrolidone, gelatin, gum arabic, polyethyleneglycol or starch, and the like. Examples of disintegrants include sodium starch glycolate or croscarmellose sodium, and the like. Examples of lubricants include magnesium stearate, light anhydrous silicic acid, talc or sodium lauryl sulfate, and the like. Examples of flavoring agents include citric acid or menthol, and the like. Examples of preservatives include sodium benzoate, sodium bisulfite, methylparaben or propylparaben, and the like. Examples of stabilizers include citric acid, sodium citrate or acetic acid, and the like. Examples of suspending agents include methylcellulose, polyvinyl pyrrolidone or aluminium stearate, and the like. Examples of dispersing agents include hydroxypropylmethylcellulose, and the like. Examples of surfactants include sodium lauryl sulfate, polaxamers, polysorbates, and the like. Examples of antioxidants include ethylene diamine tetraacetic acid (EDTA), butylated hydroxyl toluene (BHT), and the like. Examples of solubilizers include polyethylene glycols, SOLUTOL®, GELUCIRE®, and the like.

The amount of compound administered will preferably treat and reduce or alleviate the condition. A therapeutically effective amount can be readily determined by an attending diagnostician by the use of conventional techniques and by observing results obtained under analogous circumstances. In determining the therapeutically effective amount a number of factors are to be considered including but not limited to, the species of animal, its size, age and general health, the specific condition involved, the severity of the condition, the response of the patient to treatment, the particular compound administered, the mode of administration, the bioavailability of the preparation administered, the dose regime selected, the use of other medications and other relevant circumstances.

A preferred dosage will be a range from about 0.01 to 300 mg per kilogram of body weight per day. A more preferred dosage will be in the range from 0.1 to 100 mg per kilogram of body weight per day, more preferably from 0.2 to 80 mg per kilogram of body weight per day, even more preferably 0.2 to 50 mg per kilogram of body weight per day. A suitable dose can be administered in multiple sub-doses per day.

SYNTHESIS OF COMPOUNDS OF THE INVENTION

The compounds of the various embodiments may be prepared using the reaction routes and synthesis schemes as described below, employing the techniques available in the art using starting materials that are readily available. The preparation of particular compounds of the embodiments is described in detail in the following examples, but the artisan will recognize that the chemical reactions described may be readily adapted to prepare a number of other agents of the various embodiments. For example, the synthesis of non-exemplified compounds may be successfully performed by modifications apparent to those skilled in the art, e.g. by appropriately protecting interfering groups, by changing to other suitable reagents known in the art, or by making routine modifications of reaction conditions. A list of suitable protecting groups in organic synthesis can be found in T.W. Greene's Protective Groups in Organic Synthesis, 3rd Edition, John Wiley & Sons, 1991. Alternatively, other reactions disclosed herein or known in the art will be recognized as having applicability for preparing other compounds of the various embodiments.

The invention will now be illustrated by way of examples; however, the examples are not to be construed as being limitations thereto. Additional compounds, other than those described below, may be prepared using methods and synthetic protocols or appropriate variations or modifications thereof, as described herein.

EXAMPLES

In the examples described below, unless otherwise indicated, all temperatures in the following description are in degrees Celsius and all parts and percentages are by weight, unless indicated otherwise.

Various starting materials and other reagents were purchased from commercial suppliers, such as Aldrich Chemical Company or Lancaster Synthesis Ltd., and used without further purification, unless otherwise indicated. All solvents were purified by using standard methods in the art, unless otherwise indicated.

1H NMR spectra were recorded on a Bruker Avance III-500 at 500 MHZ, and 13C-NMR spectra were recorded on a Bruker Avance III-500 at 126 MHZ. When peak multiplicities are reported, the following abbreviations are used: s=singlet, d=doublet, t=triplet, m=multiplet, br=broadened, dd=doublet of doublets, dt=doublet of triplets. Coupling constants, when given, are reported in Hertz.

Mass spectra were obtained using Waters Q-TOF Premier™ Tandem Mass Spectrometer with electro-spray ionisation.

The compounds of the invention are typically synthesized from compounds synthesised in or commonly owned PCT/AU2013/000416 which published as WO2013/173862.

Example (1): Synthesis of Precursor 1 for Synthesis of Starting Material 1

Preparation of Diosgenyl-(4,6-O-(4-methoxybenzylidene)-3-benzoyl)-β-glucopyranoside (Precursor 1)

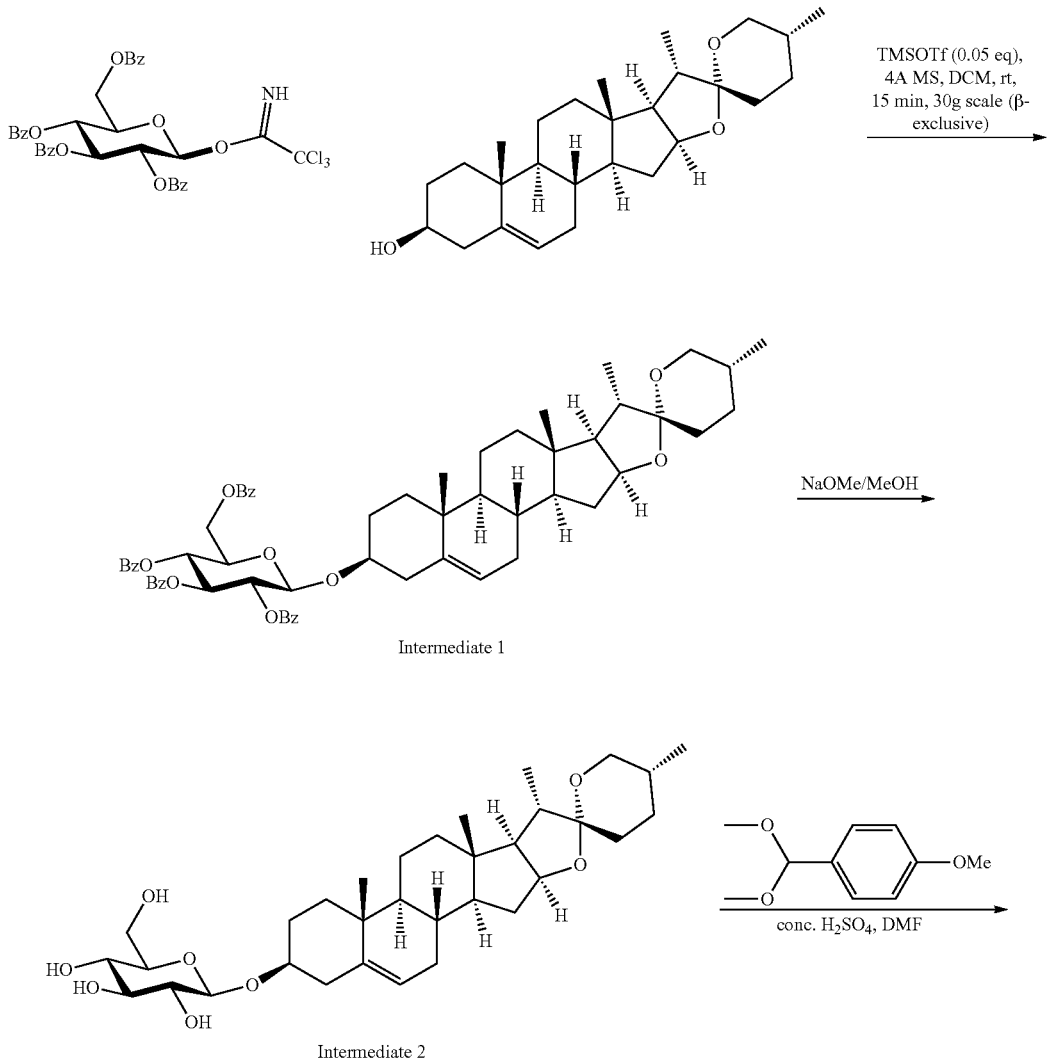

Scheme 1

-continued

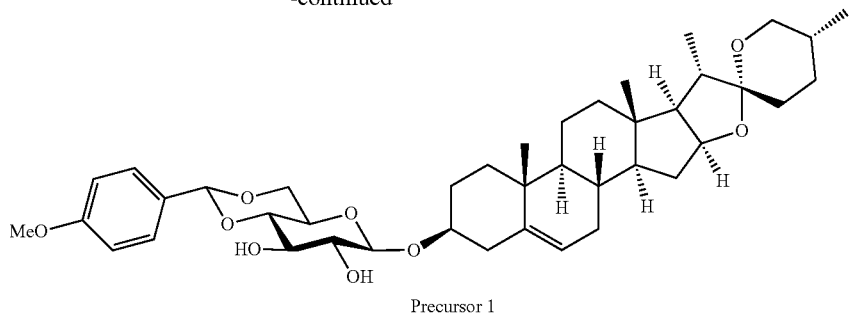

Precursor 1

Intermediate 1: Preparation of 2,3,4,6-tetra-O-benzoyl-β-D-glucopyranose (Intermediate 1)

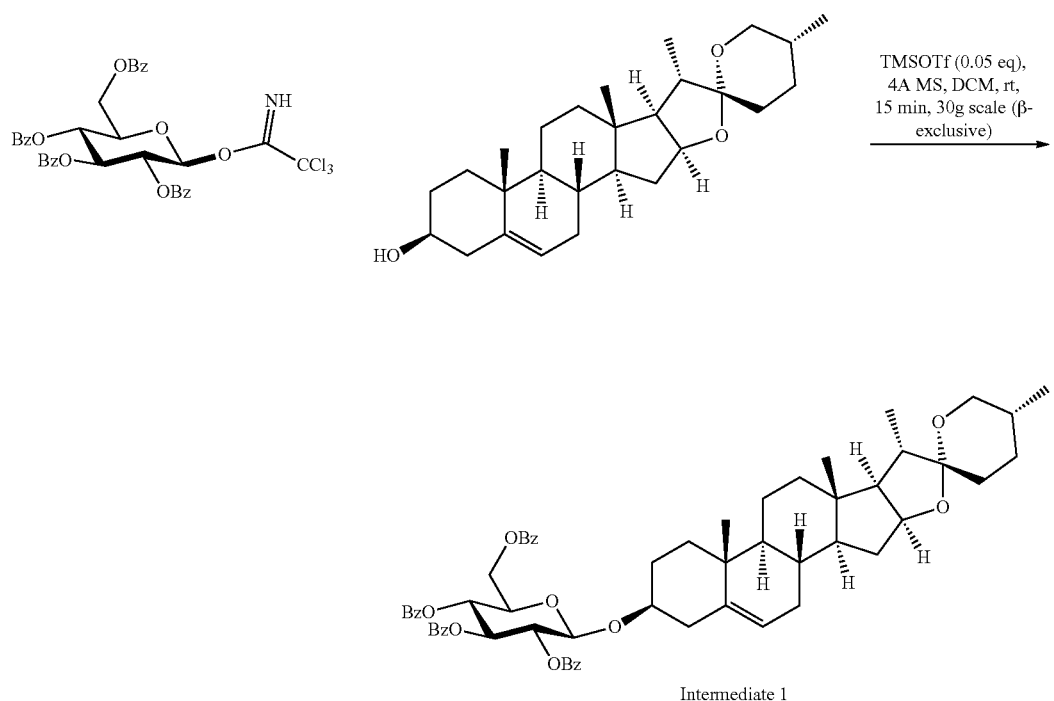

Intermediate 1

2,3,4,6-Tetra-O-benzoyl-D-glucopyranoside trichloroacetimidate (50.3 g, 67.9 mmol) and Diosgenin (26.0 g, 63 mmol) were dissolved in a mixture of dichloromethane (anhydrous, 11 mL) and toluene (anhydrous, 314 mL) and the solution dried by rotary evaporation at 40° C. The product was dissolved in dichloromethane (anhydrous, 222 mL) and cooled to 0° C. under dry nitrogen. TMSOTf (0.250 mL, 1.38 mmol) was added and the solution warmed to ambient temperature and stirred for 1 h. The reaction was then quenched with N-methylmorpholine (0.343 mL, 3.1 mmol). Additional DCM was added (20 mL) and the product precipitated by the slow addition of methanol (450 mL) and the subsequent slow addition of a mixture of methanol and water (200 mL of 3:1 methanol:water). The product was collected by filtration, washed with a mixture of methanol and water (450 mL of 4:1 methanol:water) and dried under vacuum to give diosgenyl 2,3,4,6-tetra-O-benzoyl-β-D-glucopyranose (Intermediate 1).

$^1$H NMR 500 MHz (CDCl$_3$) δ 7.81-8.03 (m, 8H), 7.23-7.56 (m, 12H), 5.89 (t, 1H, J=9.7 Hz), 5.62 (t, 1H, J=9.7 Hz), 5.49 (dd, 1H, J=7.9, 9.7 Hz), 5.22 (m, 1H), 4.94 (d, 1H, J=7.9 Hz), 4.60 (dd, 1H, J=3.4, 12.0 Hz), 4.52 (dd, 1H, J=5.9, 12.0 Hz), 4.37-4.43 (m, 1H), 4.12-4.18 (m, 1H), 3.34-3.56 (3H, M), 0.74-2.20 (m, 36H). ES-MS m/z C$_{61}$H$_{68}$O$_{12}$Na calcd 1015.4608, found 1015.4604.

Intermediate 2: Preparation of Diosgenyl-β-D-glucopyranoside (Intermediate 2)

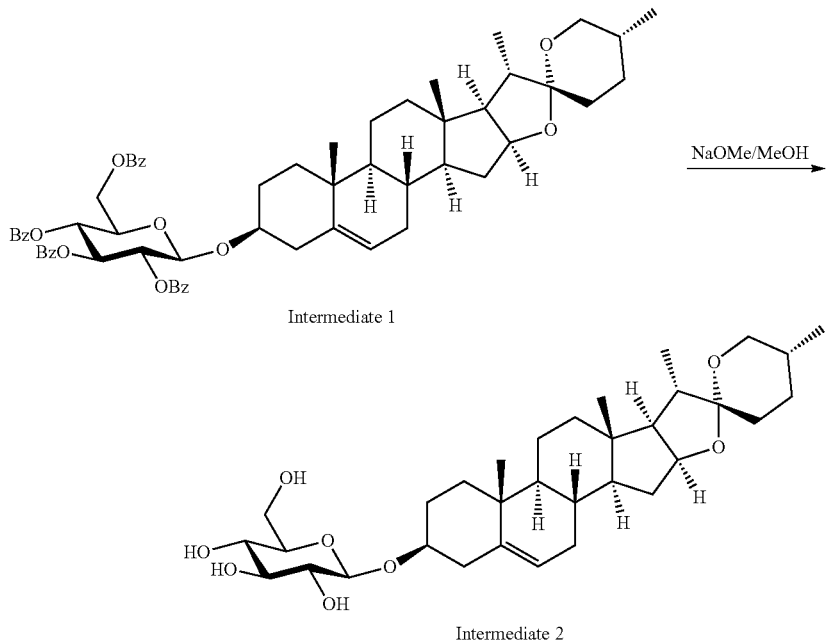

Under nitrogen, diosgenyl 2,3,4,6-tetra-O-benzoyl-β-D-glucopyranose (Intermediate 1) (59 g, 59.4 mmol) was dissolved in dichloromethane (dry, 400 mL) and methanol (dry, 400 mL). Sodium methoxide (30% in methanol, 1.9 mL, 10.1 mmol) was added and the solution stirred overnight. If during this time the pH fell below 9 then additional sodium methoxide was added. The product containing solution was neutralised with washed acidic ion-exchange resin (Amberjet 1200H). The resin was removed by filtration and any residual acidity quenched with N-methylmorpholine. The product was dried to a syrup by rotary evaporation, the syrup suspended in methanol (275 mL) to give a filterable solid which was then collected by filtration. The solid was washed with methanol (165 mL) and ethyl acetate (165 mL). The product was dried under vacuum at 30° C. to give Diosgenyl-β-D-glucopyranoside (Intermediate 2) (23.4 g, 68%) as a sesqui hydrate.

The filtrates were combined, ethyl acetate added (330 mL) and the mixture concentrated to approximately 190 mL. A second crop of product was collected by filtration and washed with ethyl acetate (100 mL). The second crop of product is further purified by column chromatography (eluent 1:9 Methanol:dichloromethane) to provide more Diosgenyl-β-D-glucopyranoside (Intermediate 2) (5.21 g, 15.2%) (total yield=28.6 g, 83.4%).

$^1$H NMR (500 MHz, 3:1 CDCl$_3$/CD$_3$OD): δ5.37 (dd, J=2.1, 3.1 Hz, 1H), 4.42 (q, J=7.4 Hz, 1H), 4.40 (d, J=7.8 Hz, 1H), 3.84 (dd, J=2.9, 12.0 Hz, 1H), 3.83 (dd, J=4.7, 12.0 Hz, 1H), 3.58 (m, 1H), 3.47 (ddd, J=2.1, 4.2, 11.6 Hz, 1H), 3.45-3.20 (m, 5H), 2.41 (ddd, J=2.1, 4.7, 13.2 Hz, 1H), 2.27 (m, 1H), 2.05-0.92 (m, 23H), 1.03 (s, 3H), 0.97 (d, J=6.9 Hz, 3H), 0.80 (d, J=6.3 Hz, 3H), 0.80 (s, 3H); $^{13}$C NMR (126 MHz, 3:1 CDCl$_3$/CD$_3$OD): δ6141.78, 123.08, 110.95, 102.51, 82.36, 80.39, 77.87, 77.25, 74.94, 71.60, 68.22, 63.38, 63.18, 57.85, 51.49, 42.99, 41.63, 41.08, 40.00, 38.57, 38.19, 33.39, 33.02, 32.78, 32.64, 31.54, 30.89, 30.00, 22.18, 20.56, 18.25, 17.50, 15.60. ES-MS m/z C$_{33}$H$_{52}$O$_8$Na calcd 599.3560, found 599.3554.

Precursor 1: Preparation of Diosgenyl-(4,6-O-(4-methoxybenzylidene)-3-benzoyl)-β-D-glucopyranoside (Precursor 1)

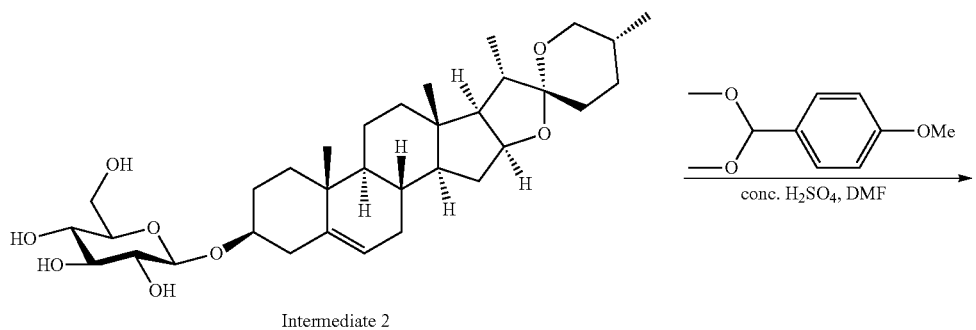

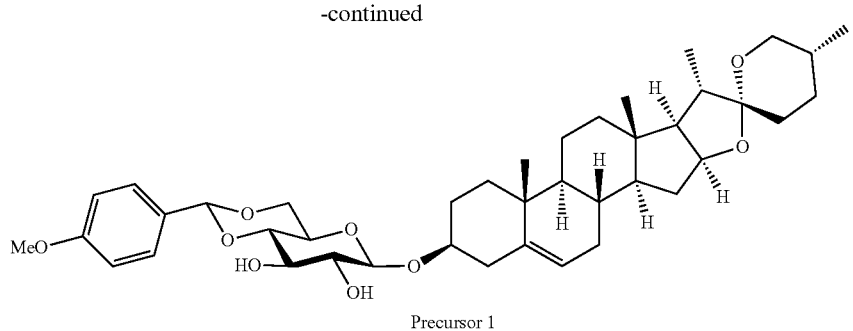

Precursor 1

To a solution of Diosgenyl-β-D-glucopyranoside (35.95 g, 62.3 mmol) in DMF (270 mL) was added anisaldehyde dimethyl acetal (42.5 mL, 249 mmol) and 5 drops of concentrated H$_2$SO$_4$, pH ~2.5. The solution was heated at 60° C. under house vacuum for 8 h to remove the methanol. The reaction was cooled and transferred to a separating funnel with ethyl acetate (400 mL), where it was washed iteratively with H$_2$O (3×300 mL), 0.5 M aqueous HCl (2×200 mL) and then sat. aq. NaHCO$_3$ (200 mL) which caused the precipitation of a grey material at interface of organic and aqueous layers.

This grey material was identified as the desired product contaminated with a small amount of DMF, and was taken up in ethyl acetate and precipitated out with hexanes to give a grey powder (13.89 g, 32%).

The ethyl acetate layer was evaporated under reduced pressure to yield an orange oil which solidified on standing.

This orange solid where dissolved in ethyl acetate and precipitated with hexanes to yield a grey powder (13.47 g, 31%).

The orange filtrate could not be induced to precipitate more product instead resulting in an oiling-out due to high 4-methoxybenzaldehyde content which acts as a solvent, so consequently was absorbed onto Celite and columned through a short silica plug eluting with a gradient of 3:1-2:1 PE/EA, then 3:1-1:1 toluene/EA to give an additional portion of yellow solid (12.62 g 29%; cumulative 39.98 g, 92%).

Example 2: Synthesis of Starting Material 1

Preparation of Diosgenyl-(2,3,4-tribenzoyl)-a-L-rhamnopyranosyl-(1→2)-3-benzoyl)-β-D-glucopyranoside (Starting Material 1)

Scheme 2

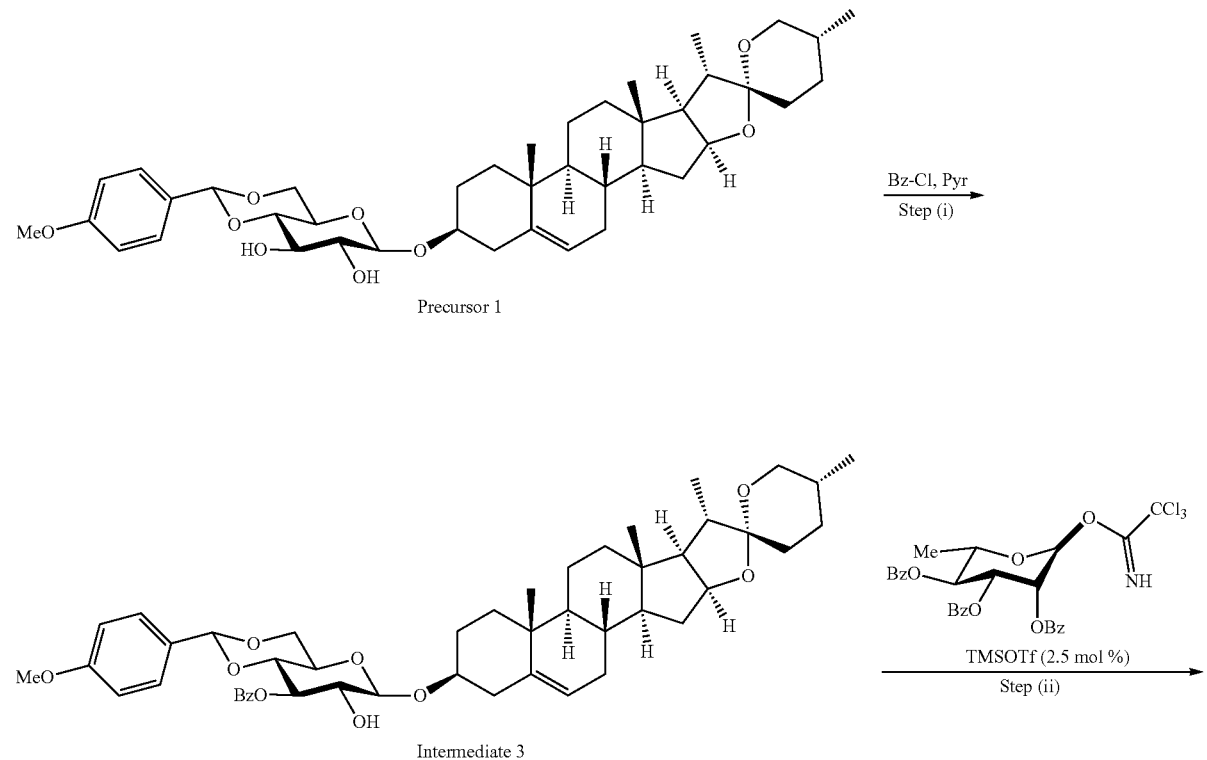

-continued
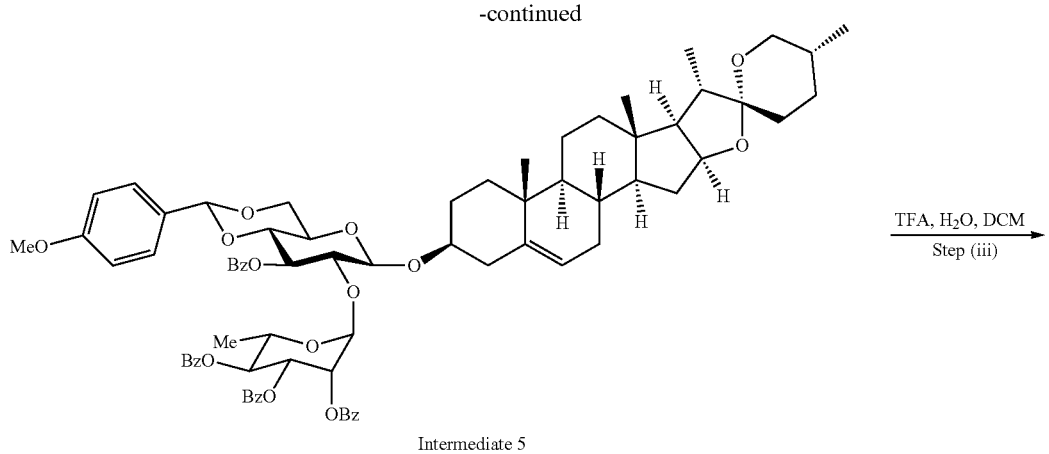
Intermediate 5
Starting material 1
Intermediate 3: Step (i)
Selective benzoylation of Precursor 1 to provide Diosgenyl-(4,6-O-(4-methoxybenzylidene)-3-benzoyl)-β-D-glucopyranoside (Intermediate 3)
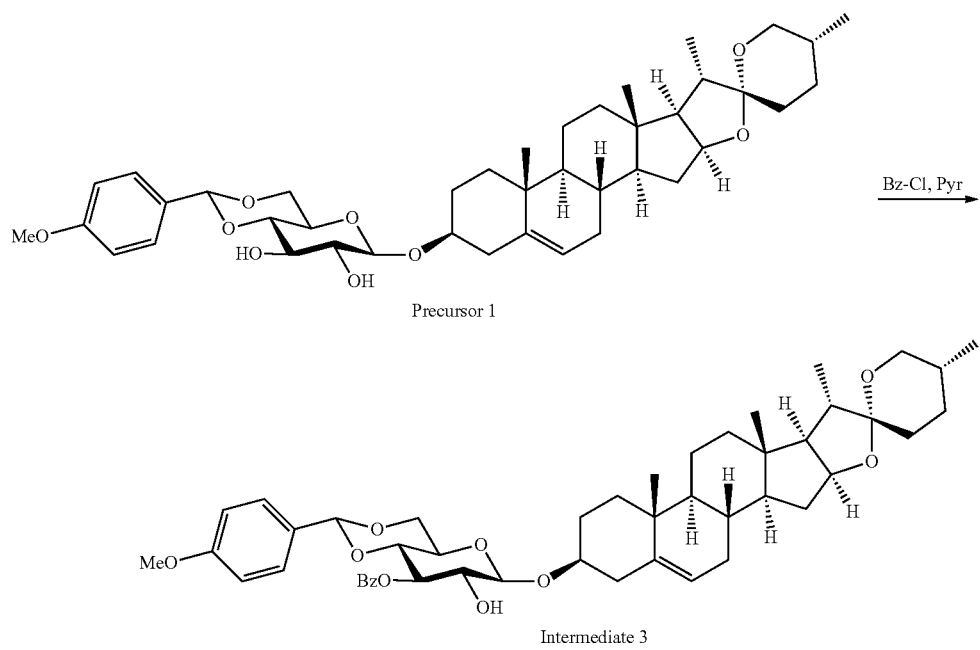
Precursor 1
Intermediate 3

To a solution of Diosgenyl-(4,6-O-(4-methoxybenzylidene)-3-benzoyl)-β-D-glucopyranoside (18.37 g, 26.4 mmol) and DMAP (0.161 g, 1.322 mmol) dissolved in pyridine (42.8 mL) and Dichloromethane (68.0 mL) cooled to −78° C. was added benzoyl chloride (3.38 mL, 29.1 mmol, 1.1 equiv) dropwise (transiently forming a chunky solid, which could be Pyr.HCl, before stirring into the reaction volume). The solution was allowed to warm to room temperature with stirring overnight.

The reaction was quenched with the addition of MeOH (10 mL), diluted with 200 mL of DCM and washed with 0.5N HCl (4×250 mL), NaHCO$_3$ (200mL), brine (200 mL), and dried with MgSO$_4$. The crude material was absorbed onto Celite evaporating with 50 mL of toluene to drive off residual DCM. This was loaded as a slurry in toluene (200 mL) to the top of a silica column and eluted with stepwise gradient of 2% EA/toluene (diBz elution), 5% EA/toluene (intermediate) and then 10% EA/toluene (monoBz).

Collected fractions were combined to yield Diosgenyl-(4,6-O-(4-methoxybenzylidene)-3-benzoyl)-β-D-glucopyranoside (Intermediate 3) (13.11, 62%). Diosgenyl-(4,6-O-(4-methoxybenzylidene)-2,3-dibenzoyl)-β-D-glucopyranoside was also isolated, 3.17 g, 13.3%.

Intermediate 5: Step (ii)

Coupling to rhamnose moiety to provide Diosgenyl-(2,3,4-tribenzoyl)-α-L-rhamnopyranosyl-(1→2)-(4,6-O-(4-methoxybenzylidene)-3-benzoyl)-β-D-glucopyranoside (Intermediate 5)

To a solution of Diosgenyl-(4,6-O-(4-methoxybenzylidene)-3-benzoyl)-β-D-glucopyranoside (Intermediate 3) (18.4g, 23.03 mmol), 2,3,4-tri-O-benzoyl-α/β-L-rhamnopyranoside trichloroacetimidate (17.87 g, 28.8 mmol, 1.25 equiv) and 4 Å MS sieves (2 g/g acceptor; 37 g) in DCM (450 mL) stirred at −78° C. was added trimethylsilyl trifluoromethanesulfonate (0.104 mL, 0.576 mmol) dropwise immediately forming a bright yellow solution. The reaction was allowed to warm room temperature overnight in the cold bath (lagged with foil) with stirring.

A small aliquot, quenched with 1 drop NEt$_3$(—yellow colour disappeared) and evaporated showed the complete consumption of starting materials by $^1$H NMR.

The reaction was quenched with addition of NEt$_3$ (2 mL) and filtered through a bed of Celite to separate the sieves. The solid support was washed with DCM (2×50 mL). Evaporation of the organic solution gave a white foam. The foam was slurried with Et$_2$O (~200 mL), filtered, and washed with cold Et$_2$O (2×50 mL) to yield Diosgenyl-(2,3,4-tribenzoyl)-α-L-rhamnopyranosyl-(1→2)-(4,6-O-(4-methoxybenzylidene)-3-benzoyl)-β-D-glucopyranoside as white powder in excellent purity (22.75 g, 79%).

The yellow filtrate was determined to be comprised of decomposed rhamnose donor and a small amount of the desired product. Absorption onto Celite and elution through silica eluting with a gradient of EA/toluene (2%, 4% then 6%) gave an additional 3.07 g (10.6%) of product (cumulative yield 25.82 g, 90%).

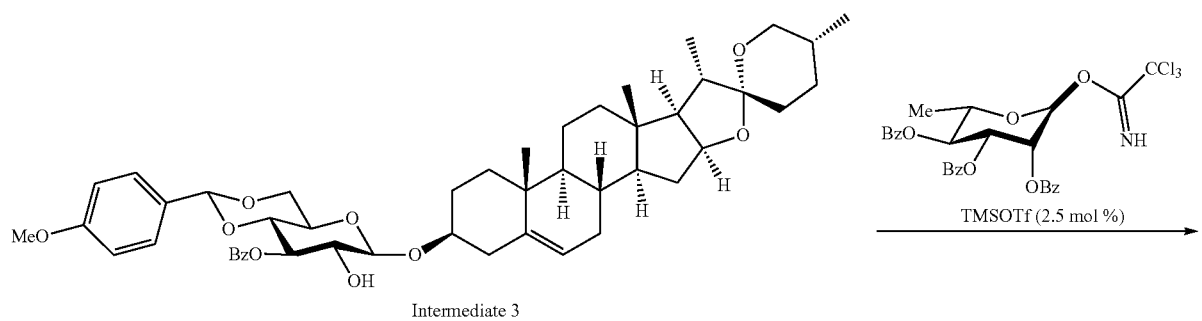

Intermediate 3

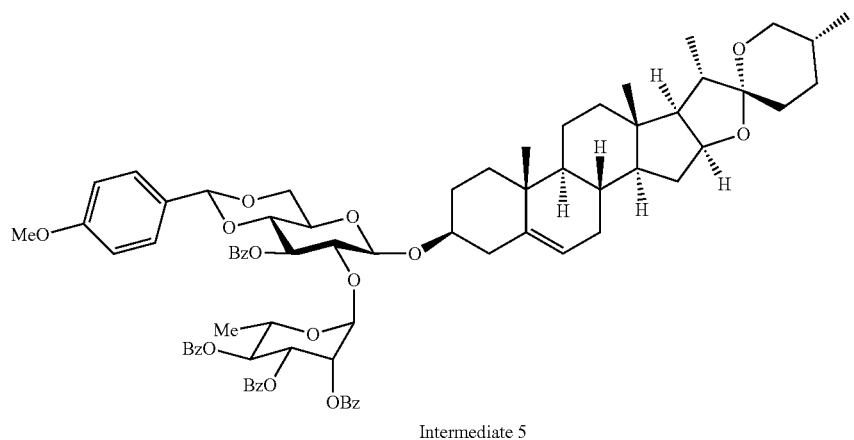

Intermediate 5

Starting Material 1: Step (iii)

Deprotection of Intermediate 5 to provide starting material 1; Diosgenyl-(2,3,4-tribenzoyl)-α-L-rhamnopyranosyl-(1→2)-3-benzoyl)-β-D-glucopyranoside (Starting material 1)

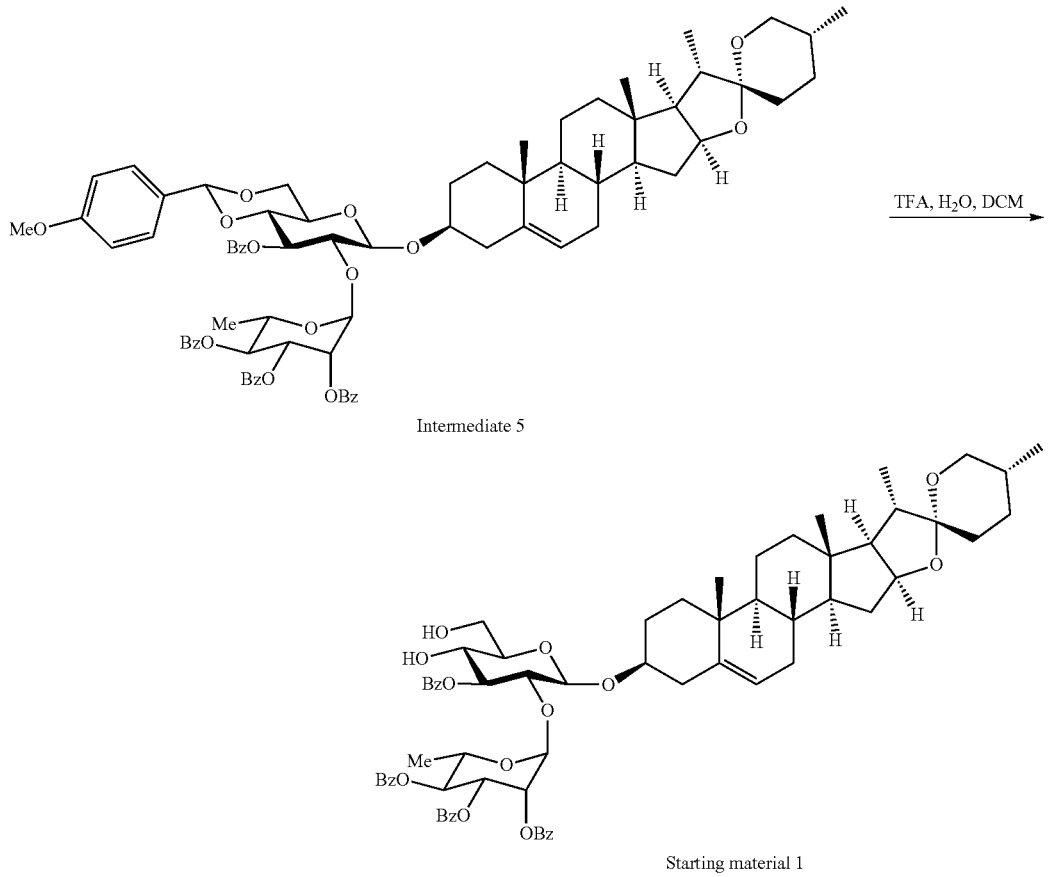

Intermediate 5

Starting material 1

Diosgenyl-(2,3,4-tribenzoyl)-α-L-rhamnopyranosyl-(1→2)-(4,6-O-(4-methoxybenzylidene)-3-benzoyl)-β-D-glucopyranoside (20 g, 15.91 mmol) was dissolved in dichloromethane (125 mL, 1943 mmol) and water (45 mL). The biphasic mixture was stirred as trifluoroacetic acid (15.91 mL) was added at 0° C. forming a bright yellow/green fluorescent coloured solution.

The reaction was allowed to stir for 3.5 hours. The reaction was quenched by washing with water (2×150 mL), NaHCO$_3$ (2×200 mL), brine (200 mL), dried with MgSO$_4$ and evaporated to give a white foam.

The crude material was dissolved in a minimum of hot EA (~30 mL) and added dropwise to a PE (500 mL) causing the precipitation of a white solid as a 'stringy' material. The solution was allowed to stir overnight resulting in the formation of a gel. Filtration gave a white solid which was washed with cold 10% EA/PE. (18.202 g, 100%).

Alternatively, Diosgenyl-(2,3,4-tribenzoyl)-α-L-rhamnopyranosyl-(1→2)-(4,6-O-(4-methoxybenzylidene)-3-benzoyl)-β-D-glucopyranoside (1.76 g, 1.43 mmol) and Amberjet® 1200 H (8.8 g) were slurried in methanol (24 mL) and tetrahydrofuran (12 mL) in a 100 mL round bottomed flask. The reaction was heated to reflux for 15 h. The reaction was then quenched with triethylamine (0.2 mL). The resin was removed by filtration and the solvent evaporated under reduced pressure. The crude product was dissolved in methanol (25 mL) and water added dropwise (15 mL) resulting in the crystallisation of a white solid. The solid product was isolated by filtration and the cake washed with 1:1 methanol/water (2×15 mL) followed by petroleum ether 60-80 (2×15 mL). The product was dried overnight under vacuum at 45° C., to give Diosgenyl-(2,3,4-tribenzoyl)-α-L-rhamnopyranosyl-(1→2)-3-benzoyl)-β-D-glucopyranoside (Starting material 1), 1.33 g, 81%.

$^1$H NMR 500 MHz (CDCl$_3$) δ 8.03 (d, 2H), 7.90 (d, 2H), 7.77 (d, 2H), 7.74 (d, 2H), 7.56 (t, J=7.5 Hz, 1H), 7.53 (t, J=7.5 Hz, 1H), 7.41 (m, 3H), 7.33 (m, 3H), 7.28 (t, J=7.5Hz, 2H), 7.23 (t, J=7.5 Hz, 2H), 5.74 (dd, J=3.6, 10.0 Hz, 1H), 5.48-5.57 (m, 3H), 5.44 (dd, J=1.6, 3.6 Hz, 1H), 5.16 (d, J=1.3 Hz, 1H), 4.82 (d, J=7.9 Hz, 1H), 4.77 (m, 1H), 4.45 (q, 1H), 3.73-3.95 (m, 6H), 3.47-3.54 (m, 2H), 3.38-3.41 (m, 2H), 2.64 (app ddd, 1H), 2.45 (t, 1H), 2.03 (m, 3H), 1.09-1.93 (m, 20H), 1.34 (d, J=6.4 Hz, 3H), 0.99 (d, J=6.4 Hz, 3H), 0.95 (s, 3H), 0.81 (d, J=6.4 Hz, 3H), 0.80 (s, 3H). $^{13}$C NMR 126 MHz (CDCl$_3$,MeOD 3:1) δ 166.3, 165.8, 165.3, 164.7, 139.9, 133.24, 133.17, 133.0. 132.9, 129.61, 129.55, 129.5, 129.3, 129.0, 128.9, 128.23, 128.17, 128.1 122.0, 109.4, 99.4, 97.6, 80.8, 79.0, 78.4, 75.9, 75.5, 71.8, 70.2, 69.6, 68.7, 66.7, 66.6, 61.9, 61.4, 56.3, 49.9, 41.4, 40.1, 39.5, 38.6, 37.0, 36.7, 32.0, 31.6, 31.3, 31.1, 30.0, 29.7, 28.5, 20.6, 19.0, 17.1, 16.8, 16.0. ES-MS m/z C$_{67}$H$_{78}$O$_{16}$Na calcd: 1161.5188, found 1161.5186

Example (3): Preparation of Starting Material 2
Preparation of Starting material 2; Diosgenyl-α-L-rhamnopyranosyl-(1→2)-β-D-glucopyranoside (Starting material 2)
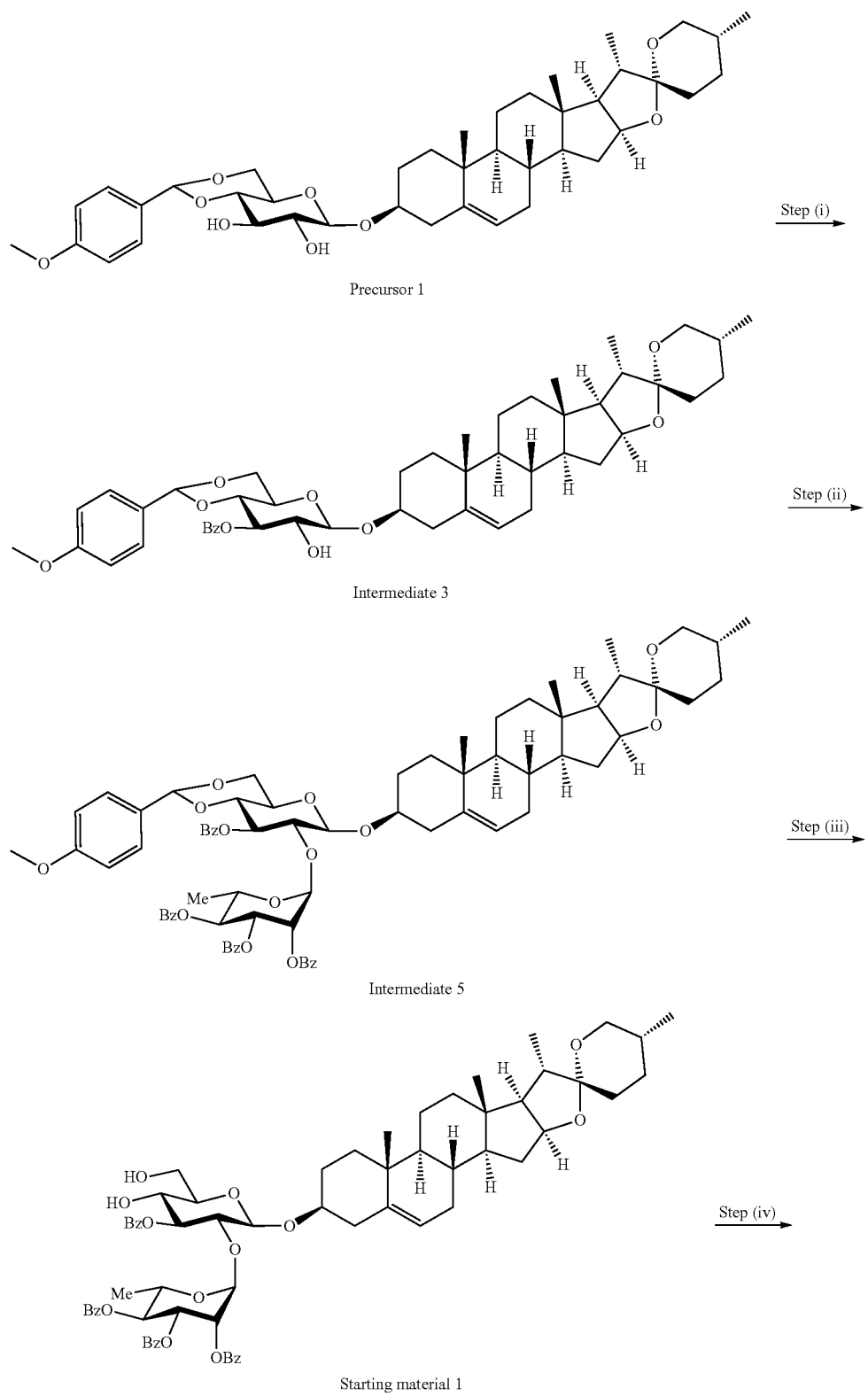

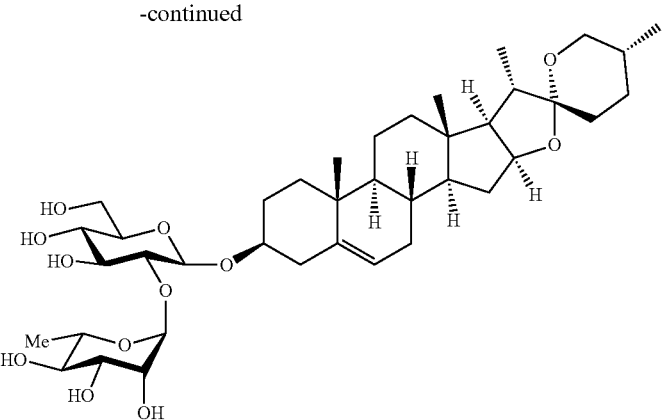

Starting material 2

As can be seen starting material 2 can be made from starting material 1. Accordingly the first three steps in the synthesis involve the same steps as in example 2.

Deprotection of starting material 1 to provide starting material 2 Diosgenyl-α-L-rhamnopyranosyl-(1→2)-β-D-glucopyranoside (starting material 2)

To a solution of Diosgenyl-(2,3,4-tribenzoyl)-α-L-rhamnopyranosyl-(1→2)-3-benzoyl)-β-D-glucopyranoside (Starting material 1) (16.542 g, 14.52 mmol) in MeOH (125 mL) was added 30 drops of NaOMe (5.4M in MeOH) and the pH was checked to be ~10. Monitoring of the mixture by TLC indicated that the reaction was complete within 90

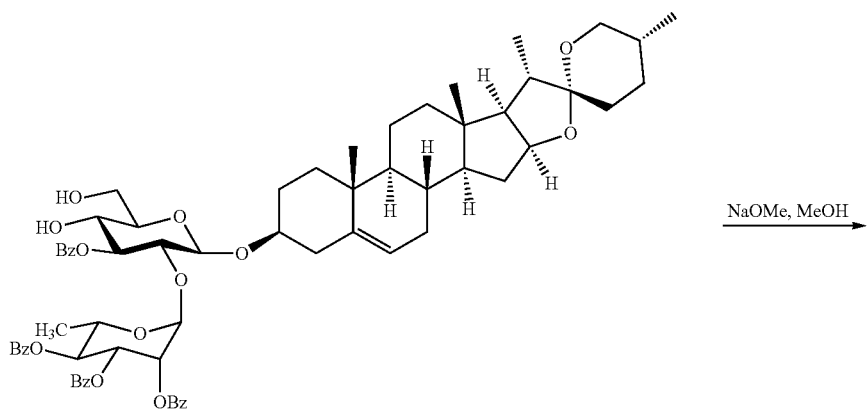

Starting material 1

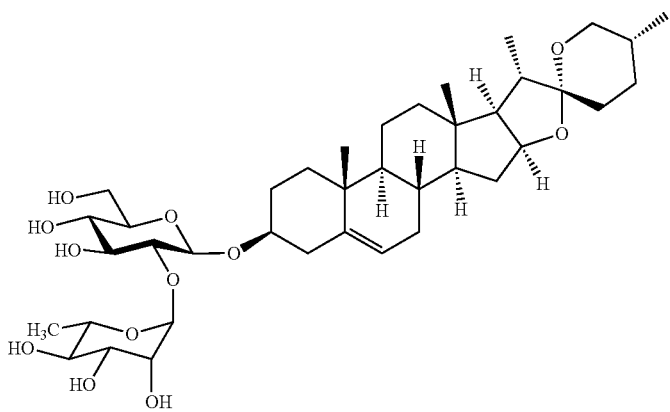

Starting material 2 mins. The reaction was quenched with the addition of DOWEX 50W-X 400 until the pH ~7 causing the DOWEX to change from a cream to light yellow colour. The resin was washed with MeOH and then 1:1 MeOH/CHCl$_3$.

The filtrate was evaporated to yield a dry white solid which was washed with EA (9.58 g, 91%). The crude material was columned on silica eluting with 10% MeOH/DCM then 20% MeOH/DCM to give starting material 2 (8.67 g, 94% pure via HPLC).

Alternatively, Diosgenyl-(2,3,4-tribenzoyl)-α-L-rhamnopyranosyl-(1→2)-3-benzoyl)-β-D-glucopyranoside (starting material 1) (9.3 g, 8.2 mmol) was dissolved in anhydrous methanol (74 mL). Sodium methoxide (0.1 mL, 30% solution in methanol) was added and the reaction mixture stirred for 22 hours at ambient temperature under argon. Tetrahydrofuran (74 mL) was added and the reaction mixture adjusted to pH 7 using Amberjet® 1200H resin. The resin was removed by filtration and washed with tetrahydrofuran (2×30 mL). The resulting solution was concentrated in vacuo and redissolved in methanol (74 mL). The product crystallized upon stirring at ambient temperature and the slurry was diluted with water (15 mL). The solid product was isolated by filtration, washed with 20% water in methanol (2×30 mL), water (30 mL) and ethyl acetate (3×30 mL). The solid product dried under vacuum at 35° C. for 16 h to afford diosgenyl-α-L-rhamnopyranosyl-(1→2)-β-D-glucopyranoside (4.65 g, 79% yield) as a white solid.

$^1$H NMR (500 MHz, 3:1 CDCl3/CD3OD): δ5.35 (dd, J=1.9, 3.2 Hz, 1H), 5.19 (d, J=1.5 Hz, 1H), 4.46 (d, J=7.6 Hz, 1H), 4.41 (q, J=7.6 Hz, 1H), 4.08 (m, 1H), 3.94 (dd, J=1.5, 3.3 Hz, 1H), 3.83 (dd, J=3.0, 12.0 Hz, 1H), 3.73 (dd, J=4.7, 12.0 Hz, 1H), 3.69 (dd, J=3.5, 9.5 Hz, 1H), 3.58 (m, 1H), 3.49 (m, 2H), 3.38 (m, 4H), 3.25 (m, 1H), 2.41 (ddd, J=1.9, 4.7, 13.4 Hz, 1H), 2.28 (m, 1H), 2.00 (m, 2H), 1.94-0.91 (m, 21H), 1.27 (d, J=6.2 Hz, 3H), 1.02 (s, 3H), 0.97 (d, J=7.3 Hz, 3H), 0.80 (d, J=6.1 Hz, 3H), 0.79 (s, 3H); 13C NMR (126 MHz, 3:1 CDCl3/CD3OD): δ141.80, 123.05, 110.94, 101.93, 100.92, 82.35, 79.97, 79.09, 76.97, 74.19, 72.66, 71.93, 71.80, 69.69, 68.23, 63.38, 63.19, 57.86, 51.53, 42.99, 41.63, 41.09, 39.71, 38.60, 38.21, 33.40, 33.03, 32.78, 32.65, 31.54, 30.89, 30.01, 22.17, 20.47, 18.55, 18.28, 17.51, 15.62; HRMS (TOF ES+) m/z calcd for C$_{39}$H$_{62}$O$_{12}$Na 745.4139, found 745.4141.

Example 4 Synthesis of Compound B and Compound B Salt

Compound B of the invention was prepared from starting material 2 in 3 steps.

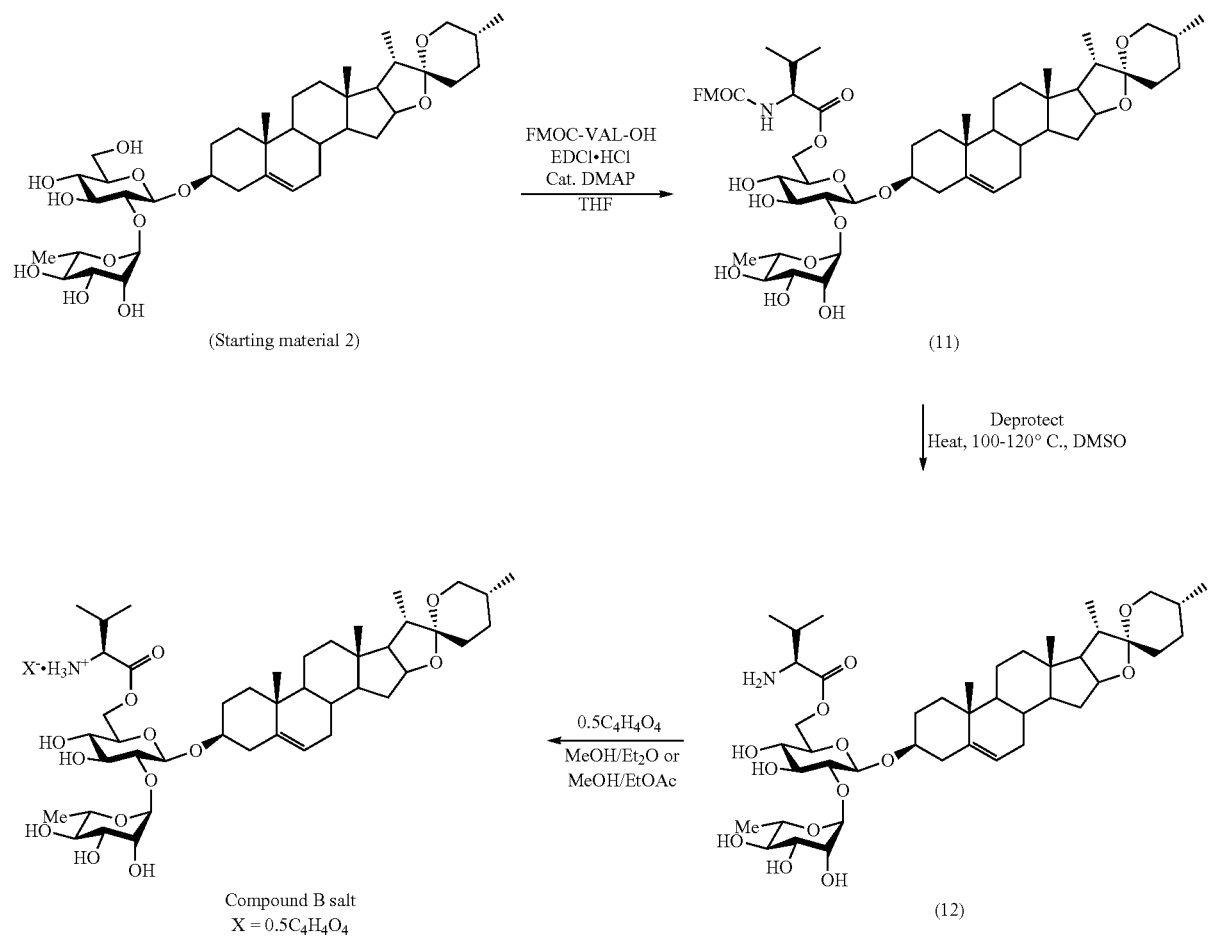

Preparation of N-FMOC-Valine Ester Analogue 11

Starting material 2 from example 3 (750 mg, 1.05 mmol), N-FMOC-valine (389 mg, 1.16 mmol, 1.1 equiv.) and N,N-dimethylaminopyridine (DMAP, 30 mg, 0.23 mmol, 0.2 equiv.) were dissolved in anhydrous THF (80-85 mL) and the mixture was cooled to 0° C. in an ice/water bath (kept under an Ar atmosphere). 1-Ethyl-3-(3-dimethylamino-propyl)carbodiimide hydrochloride salt (EDCl.HCl; 218 mg, 1.16 mmol, 1.1 equiv.) was added and the mixture was stirred on ice for two hours and then at room temperature overnight (ca. 16 hours).

The reaction was quenched by dilution with ethyl acetate (200-300 mL) and brine (100 mL). The separated brine layer was extracted with an additional aliquot of ethyl acetate (200-400 mL) and then the combined organic layers were dried (sodium sulfate), filtered and concentrated to give crude 2 plus by-products as an off-white brittle foam (~1.4 g for 750 mg reactions and 3.25 g for the 1.8 g reaction). Initially, further purification for each optimised reaction lot was conducted separately via the Biotage chromatography system (100 g SNAP KP-Sil cartridge) and with a gradient system comprising DCM/methanol as eluant (initial methanol content=3%; final methanol content=30%). Only those fractions that comprised the desired mono-FMOC-valine adduct (TLC cross-check) were combined and concentrated. At the 750 mg scale, amounts of isolable 2 were in the range 470-542 mg (43-50%).

Deprotection of (11) to give Valine Ester 'Free Base' 12 (Compound B)

A typical procedure for the thermally-mediated deprotection reaction is as follows: Intermediate 11 was dissolved in dry DMSO (1 mL per 0.1 mmol substrate; open flask) and was heated at 120° C. with stirring of the sample (an internal probe disclosed the flask reaction temperature ranged from 98-110° C.). Small aliquots of the reaction mixture were taken at 0.5, 1, 2 and 3 hours and were diluted with ethyl acetate for monitoring of progress by TLC (5:1 DCM/MeOH). All of intermediate 11 was consumed by 3 h 10 minutes. The reaction mixture was cooled to room temperature and water was added (with stirring) to give a white, gummy precipitate that was separated from liquid material by careful removal of the latter with a pipette.

The gummy material described above was then treated with ethyl acetate and hexanes to give a hygroscopic solid that was isolated on sintered glassware (NMR and TLC obtained on the mother liquors showed that this material comprised almost exclusively the dibenzofulvene fragment derived from cleavage of the FMOC moiety). The hygroscopic solid was then dissolved in methanol, concentrated and redissolved in isopropanol. Addition of hexanes to the isopropanol solution gave a precipitate; the amount generated was further optimised by cooling of the solution (refrigeration) for several hours. Precipitated material was then collected on sintered glassware to give a hygroscopic solid. An air-stable form of the material was prepared by dissolution of the solid in methanol followed by concentration under reduced pressure to give a glassy-white foam. This material was of sufficient purity (NMR, TLC) to use for the next step.

Preparation of Compound B Salt

A typical procedure is as follows: Intermediate 3 (270-320 mg) was dissolved in methanol and filtered or decanted to remove traces of any undissolved material. The solution was cooled, with stirring, in an ice-water bath and was then treated with a separately prepared methanolic solution of maleic acid (0.5 mol equiv. with respect to 3, typically 22 mg in 2 mL). The combined, homogeneous solution was then treated with diethyl ether (20 mL) but no precipitate was observed. The mixture was concentrated and then redissolved in methanol (or methanol/acetone, ~2 mL) followed by treatment with diethyl ether until just turbid. The mixture was then placed in the refrigerator to permit crystallisation to occur. Crystalline material was then collected on sintered glassware.

Example 5 Synthesis of Compound C and Compound C Salt

Compound C is prepared from starting material 1 following the scheme outlined below. In this synthesis, the primary position C-6' of starting material 1 was protected using a bulky silyl group and the remaining hydroxyl group was benzoylated. Selective cleavage of the primary silyl afforded a free alcohol which was subsequently phosphorylated. Hydrolysis of the P-chlorides followed by global deprotection using sodium methoxide gave compound C as the disodium salt.

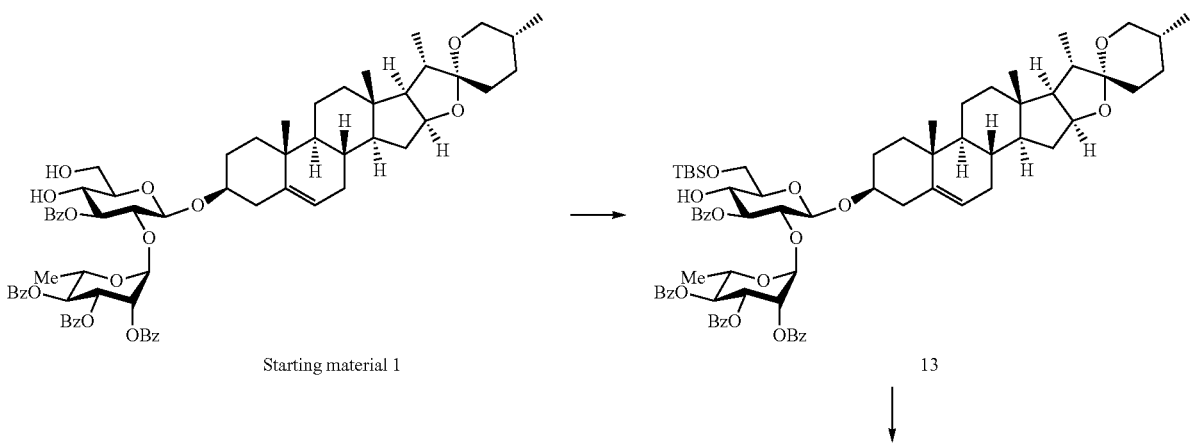

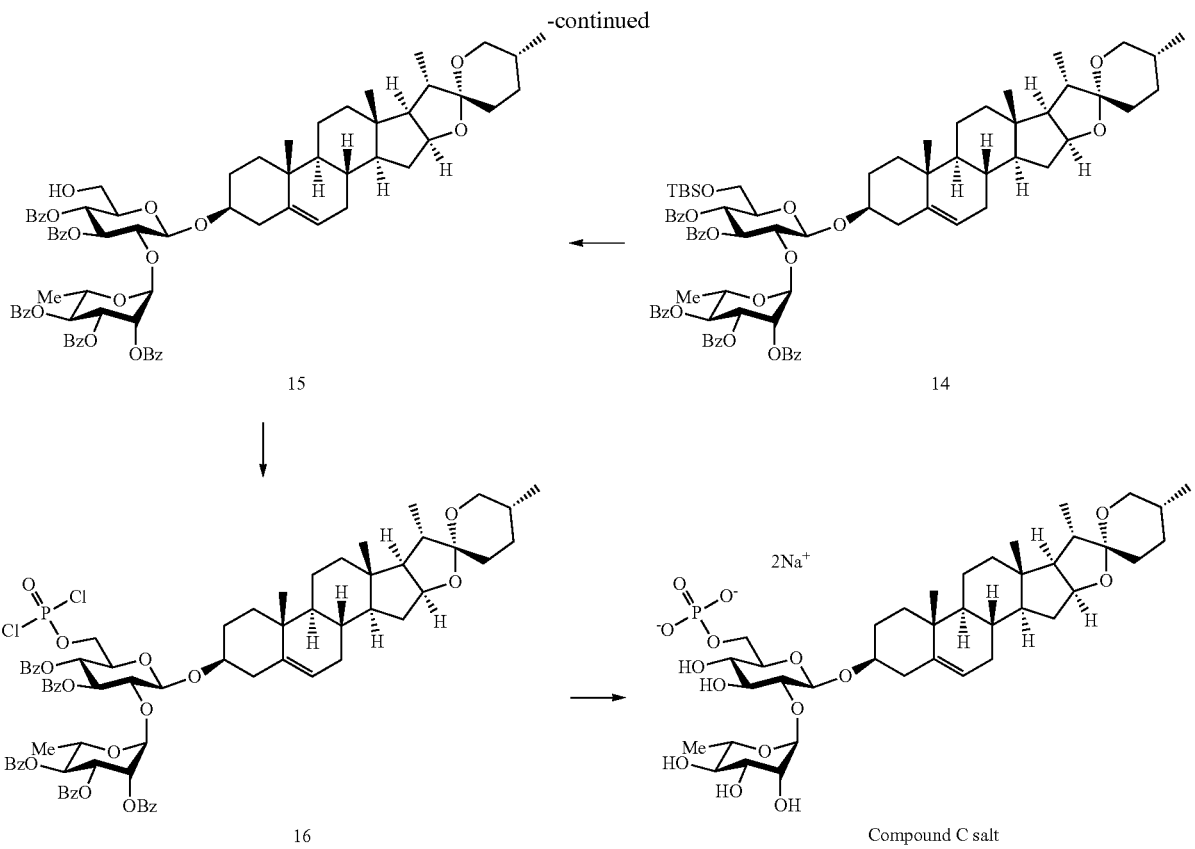

Step 1 Silylation of Starting Material 1 to Produce 13 tert-Butyldimethylsilyl chloride (1.37 g, 9.00 mmol) was added to starting material 1 (8.9 g, 7.8 mmol) and imidazole (2.69 g, 39.5 mmol) in DCM (90 mL) at 0° C. and stirred for 30 min then overnight at rt. The reaction mixture was diluted with DCM (90 mL) then washed with 7% sodium bicarbonate (200 mL) which was back extracted with DCM (100 mL). The combined organic phases were dried with anhydrous magnesium sulfate, filtered and the solvent evaporated under reduced vacuum to give compound 1 (10 g, quant.) as an off-white solid which was used in the following step with no further purification. 1H NMR (500 MHz, CDCl3) δ 8.05-8.02 (m, 2H), 7.90 (dd, J=8.4, 1.3 Hz, 2H), 7.79-7.75 (m, 2H), 7.75-7.71 (m, 2H), 7.54 (ddt, J=8.7, 7.7, 1.3 Hz, 1H), 7.51-7.47 (m, 1H), 7.42-7.24 (m, 8H), 7.23-7.19 (m, 2H), 5.74 (dd, J=10.1, 3.5 Hz, 1H), 5.57 (t, J=10.0 Hz, 1H), 5.50-5.44 (m, 2H), 5.43 (dd, J=3.5, 1.7 Hz, 1H), 5.23 (d, J=1.7 Hz, 1H), 4.76-4.71 (m, 2H), 4.43 (td, J=7.7, 6.3 Hz, 1H), 3.96-3.89 (m, 3H), 3.79-3.66 (m, 2H), 3.54 (dt, J=10.0, 5.3 Hz, 1H), 3.48 (dd, J=9.3, 4.4 Hz, 1H), 3.39 (t, J=10.9 Hz, 1H), 3.31 (d, J=3.2 Hz, 1H), 2.59 (ddd, J=13.2, 4.8, 2.3 Hz, 1H), 2.42 (t, J=12.5 Hz, 1H), 2.02 (dt, J=12.4, 6.1 Hz, 2H), 1.91-1.81 (m, 2H), 1.81-1.69 (m, 2H), 1.70-1.38 (m, 10H), 1.37-1.25 (m, 4H), 1.24-1.05 (m, 3H), 1.02-0.85 (m, 16H), 0.81-0.77 (m, 7H), 0.12-0.08 (m, 6H) ppm; 13C NMR (126 MHz, CDCl3) δ 166.94, 165.69, 165.23, 164.59, 140.18, 133.12, 132.92, 129.99, 129.78, 129.75, 129.65, 129.38, 129.29, 128.33, 128.27, 128.22, 128.15, 122.10, 109.28, 99.79, 97.78, 80.82, 79.34, 75.22, 74.99, 71.99, 71.95, 70.48, 69.63, 66.88, 66.79, 64.45, 62.19, 56.49, 50.10, 41.66, 40.31, 39.76, 38.82, 37.23, 36.89, 32.18, 31.94, 31.55, 31.46, 30.34, 29.92, 28.86, 25.89, 25.66, 20.84, 19.28, 18.33, 17.39, 17.15, 16.28, 14.54, 5.40 ppm; HRMS (ESI-pos): calcd for C73H92O16SiNa [M+Na]+ m/z 1275.6052, found m/z 1275.6062.

Benzoylation of 13

Benzoyl chloride (1.9 mL, 16 mmol) was added to crude 13 (9.8 g, 7.8 mmol) in DCM (60 mL) and pyridine (20 mL, 247 mmol) at 0° C. and stirred for 30 min then overnight at rt. The reaction mixture was quenched with saturated ammonium chloride, diluted with DCM (80 mL) washed with ammonium chloride (100 mL) which was back extracted with DCM (50 mL). The combined organic layers were washed with 7% sodium bicarbonate (200 mL), which was back extracted with DCM (50 mL). These combined organic layers were dried with anhydrous magnesium sulfate, filtered and the solvent evaporated. The resulting residue was redissolved in DCM and evaporated again to give compound 2 (10.5 g, quant.) as an off white solid which was used in the following step with no further purification. 1H NMR (500 MHz, CDCl3) δ 8.62 (dt, J=4.3, 1.8 Hz, 2H), 8.19-8.14 (m, 1H), 7.95-7.86 (m, 6H), 7.79-7.74 (m, 4H), 7.70-7.64 (m, 2H), 7.59-7.47 (m, 5H), 7.41-7.14 (m, 6H), 5.83 (t, J=9.5 Hz, 1H), 5.78 (dd, J=10.1, 3.6 Hz, 1H), 5.57 (t, J=10.0 Hz, 1H), 5.48 (dt, J=5.0, 1.8 Hz, 1H), 5.44 (dd, J=3.6, 1.7 Hz, 1H), 5.32 (t, J=9.5 Hz, 1H), 5.13 (d, J=1.7 Hz, 1H), 4.84 (d, J=7.7 Hz, 1H), 4.77 (dq, J=9.9, 6.2 Hz, 1H), 4.44 (ddd, J=8.7, 7.5, 6.4 Hz, 1H), 4.04 (dd, J=9.4, 7.7 Hz, 1H), 3.83-3.71 (m, 3H), 3.48 (ddd, J=10.9, 4.4, 2.0 Hz, 1H), 3.39 (t, J=10.9 Hz, 1H), 2.62 (ddd, J=13.2, 4.8, 2.2 Hz, 1H), 2.50-2.40 (m, 1H), 2.12-1.98 (m, 3H), 1.92-1.83 (m, 2H), 1.83-1.56 (m, 9H), 1.56-1.40 (m, 2H), 1.34 (d, J=6.2 Hz, 3H), 1.26-1.06 (m, 3H), 1.06-0.89 (m, 8H), 0.86 (s, 9H), 0.82-0.77 (m, 7H), 0.02 (d, J=1.2 Hz, 6H) ppm; 13C NMR (126 MHz, CDCl3) δ 165.67, 165.51, 165.43, 165.26, 164.60, 149.88, 140.14, 135.89, 134.51, 133.21, 133.17, 133.09, 132.92, 132.84, 130.57, 129.86, 129.83, 129.79, 129.74, 129.71, 129.66, 129.40, 129.20, 129.19, 129.14, 128.96, 128.88, 128.40, 128.36, 128.33, 128.26, 128.16, 128.06, 123.70, 122.12, 109.27, 99.83, 97.64, 80.82, 79.35, 75.65, 75.61, 75.23, 71.96, 70.47, 69.93, 69.65, 66.87, 66.76, 63.04, 62.20, 56.48, 50.11, 41.66, 40.31, 39.75, 38.82, 37.24, 36.90, 32.18, 31.94, 31.57, 31.46, 30.33, 29.91, 28.86, 25.83, 20.84, 19.27, 18.30, 17.37, 17.15, 16.29, 14.54, 5.35, 5.39 ppm; HRMS (ESI-pos): calcd for C80H96O17SiNa [M+Na]+m/z 1379.6315, found m/z 1379.6313.

Desilylation of 14

Acetyl chloride (5.3 mL, 74 mmol) was added to crude 14 (10.0 g, 7.4 mmol) in DCM (100 mL) and methanol (50 mL) at 0° C. and stirred for 90 min at 0° C. The reaction mixture was then quenched with 7% sodium bicarbonate (150 mL). The aqueous layer was back extracted with DCM (100 mL) and the organic phases were combined, dried with anhydrous magnesium sulfate, filtered and the solvent evaporated. The crude residue was taken up in DCM and purified by column chromatography (silica, ethyl acetate/heptane, 1:6 to 2:5) to give compound 3 (8.3 g, 90%) as a white foam. 1H NMR (500 MHz, CDCl3) δ 7.97-7.88 (m, 6H), 7.78-7.72 (m, 4H), 7.55-7.46 (m, 3H), 7.41-7.35 (m, 5H), 7.35-7.16 (m, 6H), 5.92 (t, J=9.6 Hz, 1H), 5.77 (dd, J=10.1, 3.5 Hz, 1H), 5.57 (t, J=10.1 Hz, 1H), 5.46 (ddd, J=17.0, 3.5, 1.8 Hz, 2H), 5.35 (t, J=9.6 Hz, 1H), 5.16 (d, J=1.7 Hz, 1H), 4.89 (d, J=7.7 Hz, 1H), 4.76 (dq, J=9.9, 6.3 Hz, 1H), 4.43 (ddd, J=8.6, 7.6, 6.4 Hz, 1H), 4.08 (dd, J=9.5, 7.7 Hz, 1H), 3.86-3.67 (m, 4H), 3.48 (ddd, J=10.8, 4.5, 1.9 Hz, 1H), 3.39 (t, J=11.0 Hz, 1H), 2.62 (ddd, J=13.2, 4.9, 2.3 Hz, 1H), 2.53 (dd, J=8.9, 5.1 Hz, 1H), 2.50-2.42 (m, 1H), 2.10-1.98 (m, 2H), 1.92-1.84 (m, 2H), 1.82-1.38 (m, 10H), 1.37-1.08 (m, 9H), 1.04-0.93 (m, 7H), 0.91-0.86 (m, 2H), 0.80 (d, J=6.5 Hz, 6H) ppm; 13C NMR (126 MHz, CDCl3) δ 166.37, 165.68, 165.45, 165.29, 164.61, 140.06, 133.64, 133.21, 133.14, 132.98, 130.01, 129.85, 129.79, 129.72, 129.67, 129.37, 129.25, 129.02, 128.61, 128.51, 128.34, 128.27, 128.18, 128.14, 122.29, 109.28, 99.92, 97.69, 80.82, 79.48, 75.30, 75.08, 74.43, 71.88, 70.44, 69.68, 69.61, 66.87, 62.18, 61.45, 56.48, 50.07, 41.66, 40.31, 39.73, 38.79, 37.18, 36.91, 32.18, 31.94, 31.89, 31.54, 31.46, 30.33, 29.95, 29.02, 28.85, 22.69, 20.84, 19.29, 17.37, 17.15, 16.28, 14.54, 14.11 ppm; HRMS (ESI-pos): calcd for C74H82O17Na [M+Na]+ m/z 1265.5450, found m/z 1265.5442.

Phosphorylation of 15

Phosphorus oxychloride (1.2 g, 7.8 mmol) was added dropwise to 15 (8.0 g, 6.4 mmol) and N methylmorpholine (1.2 g, 12 mmol) in dry DCM (80 mL), in a water bath, and stirred at rt overnight. The mixture was then diluted with heptane (240 mL). After stirring at 0° C. for 10 min, the yellow precipitate was filtered off through cotton wool and washed with 3:1 heptane/DCM. The organic solution was extracted with ice cold 0.1 M HCl (200 mL), then twice with ice cold water (200 mL each). The organic phase was dried with anhydrous magnesium sulfate, filtered and the solvent evaporated under reduced vacuum to give compound 4 (8.3 g, 94%) as an off-white solid which was used in the following step with no further purification. 1H NMR (500 MHz, CDCl3) δ 7.94-7.86 (m, 6H), 7.78-7.73 (m, 4H), 7.56-7.46 (m, 3H), 7.41-7.35 (m, 7H), 7.35-7.16 (m, 5H), 5.88 (t, J=9.5 Hz, 1H), 5.76 (dd, J=10.1, 3.5 Hz, 1H), 5.58 (t, J=10.0 Hz, 1H), 5.46 (ddd, J=21.9, 3.7, 1.8 Hz, 2H), 5.33 (t, J=9.8 Hz, 1H), 5.16 (d, J=1.7 Hz, 1H), 4.90 (d, J=7.7 Hz, 1H), 4.74 (dq, J=9.9, 6.2 Hz, 1H), 4.55-4.38 (m, 3H), 4.13-4.03 (m, 2H), 3.76 (tt, J=11.3, 4.7 Hz, 1H), 3.48 (ddd, J=10.9, 4.4, 2.0 Hz, 1H), 3.39 (t, J=10.9 Hz, 1H), 2.61 (ddd, J=13.2, 4.8, 2.3 Hz, 1H), 2.51-2.40 (m, 1H), 2.04 (dddd, J=24.7, 13.1, 6.1, 4.0 Hz, 3H), 1.94-1.82 (m, 2H), 1.82-1.57 (m, 6H), 1.57-1.38 (m, 3H), 1.38-1.09 (m, 9H), 1.05-0.92 (m, 6H), 0.88 (t, J=7.0 Hz, 2H), 0.80 (d, J=5.9 Hz, 6H) ppm; 13C NMR (126 MHz, CDCl3) δ 165.65, 165.58, 165.36, 165.29, 164.63, 139.97, 133.73, 133.23, 133.17, 133.09, 132.99, 129.95, 129.87, 129.78, 129.71, 129.66, 129.34, 129.23, 129.20, 128.82, 128.55, 128.38, 128.35, 128.29, 128.19, 128.16, 122.34, 109.27, 100.19, 97.71, 80.82, 80.14, 75.15, 74.81, 72.22, 72.14, 71.81, 70.38, 69.81, 69.74, 69.57, 69.32, 66.93, 66.87, 62.17, 56.46, 50.00, 41.66, 40.31, 39.71, 38.88, 37.14, 36.87, 32.17, 31.94, 31.89, 31.55, 31.46, 30.33, 29.93, 29.01, 28.86, 22.69, 20.83, 19.27, 17.37, 17.15, 16.28, 14.54, 14.10 ppm; 31P-NMR (202 MHz, CDCl3) ☐ 7.8 ppm; HRMS (ESI-pos): calcd for C74H81O18Cl2PNa [M+Na]+ m/z 1381.4435, found m/z 1381.4441.

Solvolysis of 16

Sodium bicarbonate (75 mL, 7% solution) was added to 16 (8.0 g, 5.9 mmol) in DCM (75 mL) and the biphasic mixture was stirred vigorously over three nights at 30° C. (reaction monitored by MS). The DCM layer was isolated and the aqueous layer was back extracted with DCM (75 mL) and the organic phases were combined, dried with anhydrous magnesium sulfate, filtered and the solvent evaporated to give the organophosphate of 16 (quant.). HRMS (ESI neg): calcd for C74H82O20P [M−H]− m/z 1321.5137, found m/z 1321.5134.

Half of this material (4.1 g, 3.1 mmol) was dissolved in THF (170 mL). To this solution, sodium methoxide in methanol (1.2 mL, 5.4 M, 6.5 mmol) was added and the resulting suspension was stirred overnight at rt. The reaction was quenched with water (50 mL), forming a clear solution, and the THF was carefully removed under reduced pressure. The white suspension was diluted to 250 mL with water and centrifuged for 2 min at 3 g. The supernatant was decanted and purified by column chromatography (C18 silica, acetonitrile/water, 1:3), guided by HPLC, to give ORIL019 (1.1 g, 43%) as a white solid following lyophilisation. 1H NMR (500 MHz, MeOH-d4, pH 7, 13 mg/mL) δ 5.38 (dt, J=4.2, 2.0 Hz, 1H), 5.23 (d, J=1.8 Hz, 1H), 4.46 (d, J=7.8 Hz, 1H), 4.44-4.36 (m, 1H), 4.21-4.08 (m, 2H), 3.99-3.89 (m, 2H), 3.70-3.59 (m, 2H), 3.59-3.47 (m, 2H), 3.47-3.36 (m, 3H), 3.31 (p, J=1.6 Hz, 8H), 3.24 (dt, J=9.5, 2.8 Hz, 1H), 2.43 (ddd, J=13.3, 4.8, 2.2 Hz, 1H), 2.34-2.24 (m, 1H), 1.99 (dddd, J=17.0, 13.2, 6.1, 4.3 Hz, 2H), 1.94-1.82 (m, 3H), 1.79-1.72 (m, 2H), 1.72-1.37 (m, 8H), 1.34-1.11 (m, 6H), 1.04 (s, 4H), 0.96 (d, J=6.9 Hz, 4H), 0.86-0.73 (m, 6H) ppm; 13C NMR (126 MHz; MeOH-d4, pH 7, 13 mg/mL) δ 141.97, 122.64, 110.61, 102.17, 100.95, 82.26, 79.41, 78.59, 77.38, 74.05, 72.43, 72.28, 70.91, 69.74, 67.90, 64.34, 63.81, 57.85, 51.76, 42.97, 41.47, 40.98, 39.61, 38.63, 38.09, 33.23, 32.87, 32.80, 32.49, 31.49, 30.78, 29.95, 22.04, 19.89, 18.04, 17.52, 16.81, 14.91 ppm; 31P-NMR (202 MHz, MeOH-d4, pH 7, 13 mg/mL) δ 6.0 ppm; HRMS (ESI-pos): calcd for C39H63O15PNa [M+2H−Na]+ m/z 825.3802, found m/z 825.3806; HRMS (ESI-neg): calcd for C39H62O15P [M+H−2Na]− m/z 801.3826, found m/z 801.3820.

Example 6 Biological Testing-Haemolysis Assay

Haemolysis is a clinical condition where the red cell membrane is irreversibly damaged causing the release of its haemoglobin content. The in vitro haemolysis assay is a simple test to determine the haemolytic potential of a test substance on isolated and washed red blood cells.

In this example three compounds identified as compound A, compound C disodium salt and compound B ½ maleate salt and Saponin from Quillaja bark (S4521) were tested for haemolytic potential using washed human erythrocytes. The compounds were tested over a dose curve with a maximum concentration of 100 pg/mL and a lowest concentration of 0.781 pg/mL. The concentration range is 100-0.781 pg/mL.

1. Blood Preparation

Briefly, whole blood (40 mL) was collected from a single human volunteer into multiple EDT vacutainer tubes. The red blood cells (RBC) were washed and isolated from plasma components by three centrifugations at 3000 rpm for 5 minutes in isotonic 0.9% sodium chloride. After the final wash, 0.1 mL volumes of red blood cells were added to each treatment tube.

2. Preparation of Test Solutions

The test compounds compound A, compound C disodium salt and compound B ½ maleate salt and the reference article (Saponin S4521) were initially formulated as 100× stock solutions at a concentration of 10 mg/mL in the appropriate diluents (DMSO for compounds, 0.9% NaCl for Saponin S4521). These stock solutions were then further diluted 1:100 in 0.9% NaCl to prepare the highest concentration of 100 pg/mL in 1% DMSO/NaCl. The highest concentration solutions were further diluted serially 1:2 in 1% DMSONaCl to achieve lower concentrations of 50, 25, 12.5, 6.25, 3.125, 1.562 and 0.781 pg/ml of active component.

3. Control Article Formulation

The positive control article (hypertonic solution of 5ll/1 NaCl) was formulated by weighing 2.92 g NaCl in 10 mL MilliQ water. The negative control article (isotonic solution of 0.154M NaCl) was formulated on the day of use by dissolving 0.09 g NaCl into 10 mL MilliQ water. The vehicle used to dilute the test articles, 1% DMSO/NaCl, was used as the reagent blank in the assay.

4. Methodology

Tubes containing cells and treatments were incubated at 37° C. with gentle agitation in an orbital mixer for 3 hours. At completion of the incubation, tubes were centrifuged at 3000 rpm for 5 minutes and 200 ptL aliquots of supernatant from each tube were transferred to a 96-well microplate for measurement of absorbance at 535 nm. A layout for the 96-Nell microplate is presented in Appendix 1. A 1% DMSO/NaCl vehicle in the absence of blood was used as the reagent blank in the assay.

5. Data Collection and Analysis

Mean values for the negative (0.154M NaCl), positive (5M NaCl) and blank triplicate wells were determined. These were then used to calculate the % haemolysis for each sample according to the following formula:

$$\% \text{ haemolysis} = \frac{(\text{Sample Blank}) - \text{negative control Blank}) \times 100}{(\text{positive control blank}) - \text{negative control blank}}$$

Calculations of 50% haemolytic dose (HD50) was performed by non-linear regression analyses using a log(agonist) vs normalized response variable slope curve fit on GraphPad Prism for Mac OS X (Version 5.0c, GraphPad Software, California, USA).

6. Results

The positive control (5M NaCl) treatment and negative control (0.154M NaCl) treatments resulted in mean OD535 values of 3.442 (Plate 1) or 3.472 (Plate 2) and 0.100 (Plate 1) or 0.126 (Plate 2) respectively which were identified as the 100% and 0% haemolysis values.

Treatment with each test compound resulted in a dose-dependent increase in haemolysis. Saponin from Quillaja bark (S4521) showed the highest haemolytic activity, with a 50% haemolytic dose (HD50) value of 7.35 µg/ml. Amongst the test compounds, A showed the highest haemolytic activity with a HD50 value of 31.57 µg/ml. C disodium salt and B half maleate salt showed lower haemolytic activity in this assay with HD50 values of 145.70 µg/ml and 73.55 µg/ml, respectively.

Haemolysis Summary

| Treatment | $HD_{50}$ (µg/ml) |
|---|---|
| A | 31.57 |
| B half maleate salt | 73.55 |
| C disodium salt | 145.70 |
| Saponinin (S4521) | 7.35 |

The full results for percent haemolysis for all samples were as follows:

| Concentration (µg/ml) | Compound A | Compound B half maleate salt | Compound C disodium salt | Saponin |
|---|---|---|---|---|
| 100 | 103.2 | 102.3 | 51.9 | 102.0 |
| 50 | 86.7 | 102.3 | 2.9 | 101.9 |
| 25 | 36.0 | 1.6 | 1.8 | 101.1 |
| 12.5 | 13.4 | 0.2 | 0.5 | 101.1 |
| 6.25 | 3.2 | 0.3 | 1.6 | 16.9 |
| 3.125 | −0.1 | −0.1 | 0.5 | −0.1 |
| 1.562 | 0.5 | −0.2 | 1.9 | −0.1 |
| 0.781 | −0.3 | 1.4 | 1.0 | 0.2 |

Example 7 Biological Testing—Cell Growth Inhibition Assay

Duplicate experiments were performed using the CellTiter-Blue® Cell Viability Assay to determine IC50 values for Compound A, Compound B and Compound C against each cell line. The general methodology for preparation of test articles described in Example 6 was used. The test compounds compound A, compound C disodium salt and compound B ½ maleate salt were initially formulated as 100× stock solutions at a concentration of 10 mg/mL in the appropriate diluents (DMSO for compounds). These stock solutions were then further diluted in cell culture medium to achieve lower concentrations of 100, 50, 25, 12.5, 6.25 and 3.125, 1.563, 0.781, 0.390 and 0.195 µM of active component. The specific cancer cells were A549, HCT 116, MCF-7 and MIA PaCa-2.

Cell Lines

Human cancer cell types were: HTC-116 (colon); A549 (Lung); HT29 (colon); MCF-7; Mia PaCa-2 (pancreas)

(i) Cell Culture and Cell Growth Assay

Cells were seeded in duplicate at 3-4,000 per microtitre well in 50 µl of cell culture medium . After 24 hours, 50 µL of test article or vehicle control prepared in medium at 2× required concentration were added to each well. Cancer cells were allowed to grow in the presence of drug for 48 hours before cell growth relative to untreated control wells was determined with CellTiter-Blue® Cell Viability Assay.

Calculation of $IC_{50}$ Values

IC50 values were calculated using Prism 6 for Mac OS X using a nonlinear regression (log(inhibitor) vs. response—Variable slope (four parameters)

The results for cell inhibition growth, expressed as $IC_{50}$ values are as follows.

| Cell Line | | Compound A | Compound B | Compound C |
|---|---|---|---|---|
| A549 | Experiment 1 | 4.74 | 9.86 | 2.46 |
| | Experiment 2 | 3.60 | 10.47 | 1.53 |
| | Average ± SEM | 4.17 ± 0.57 | 10.17 ± 0.31 | 2.00 ± 0.47 |
| HCT 116 | Experiment 1 | 5.17 | 11.68 | 4.08 |
| | Experiment 2 | 5.02 | 13.11 | 1.99 |
| | Average ± SEM | 5.10 ± 0.08 | 12.40 ± 0.72 | 3.04 ± 1.05 |
| MCF-7 | Experiment 1 | 7.91 | 14.65 | 5.45 |
| | Experiment 2 | 7.38 | 15.28 | 2.88 |
| | Average ± SEM | 7.65 ± 0.27 | 14.97 ± 0.32 | 4.17 ± 1.29 |
| MIA PaCa-2 | Experiment 1 | 6.17 | 11.16 | 3.52 |
| | Experiment 2 | 5.08 | 7.62 | 2.55 |
| | Average ± SEM | 5.63 ± 0.55 | 9.39 ± 1.77 | 3.04 ± 0.49 |
| PC-3 | Experiment 1 | 6.42 | 12.36 | 4.32 |
| | Experiment 2 | 5.85 | 10.96 | 2.18 |
| | Average ± SEM | 6.14 ± 0.29 | 11.66 ± 0.70 | 3.25 ± 1.07 |

Example 8 Biological Testing—Immune Response Activity

Groups of four C57 female mice were injected into both flanks with a regime selected from phosphate buffered saline (PBS) solutions of (i) 100 μg of Ovalbumin protein (OVA) (ii) 100 μg of Ovalbumin protein (OVA) in combination 20 μg of saponin or (iii) 100 μg of Ovalbumin protein (OVA) in combination 20 μg of compound C disodium salt (200 μl, final volume in each case). Five days post-immunization, the thickness of both ears was measured with calipers, and then the right ears were challenged (injected) with 15 μg OVA in phosphate-buffered saline (PBS, 20 μl), and the left ears were challenged (injected) with PBS alone as a negative control. The thickness of right and left ears were assessed one and two days after challenge for evidence of swelling due to contact hypersensitivity.

As can be seen by reference to FIG. 1 the compound C disodium salt had similar ability to elicit an immune response as the known immune response modifier (saponin) in contrast to the phosphate buffered saline which had no statistically significant effect.

Finally, it will be appreciated that various modifications and variations of the methods and compositions of the invention described herein would be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention that is apparent to those skilled in the art are intended to be within the scope of the present invention.

The invention claimed is:

1. A compound of the formula (I)

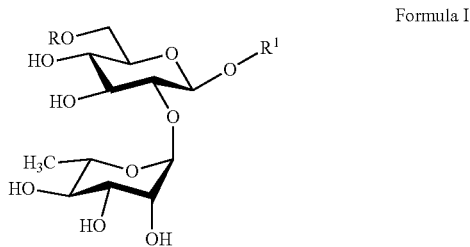

Formula I wherein
R is a moiety containing either (1) at least one a hydrogen ion donor, (2) at least one hydrogen ion acceptor or (3) a combination thereof; and
$R^1$ is a group of Formula E, F or G:

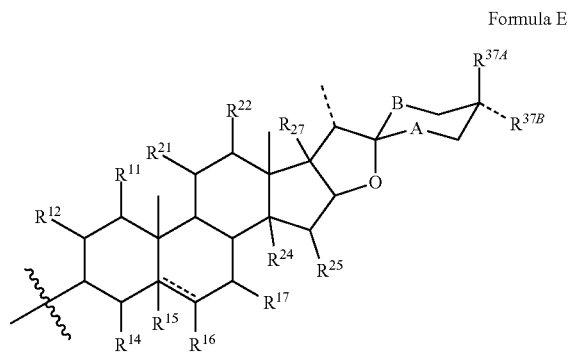

Formula E wherein
$R^{11}$, $R^{12}$, $R^{14}$, $R^{16}$, $R^{17}$, $R^{21}$, $R^{22}$, $R^{24}$, $R^{25}$ and $R^{27}$ are independently H, OH, =O, pharmacologically acceptable ester groups or pharmacologically acceptable ether groups;
$R^{15}$ is H when C-5,C-6 is a single bond, and nothing when C-5,C-6 is a double bond;
A is either O concurrently with B being $CH_2$, or B is O concurrently with A being $CH_2$;
$R^{37A}$ is H concurrently with $R^{37B}$ being $CH_3$, or $R^{37A}$ is $CH_3$ concurrently with $R^{37B}$ being H;

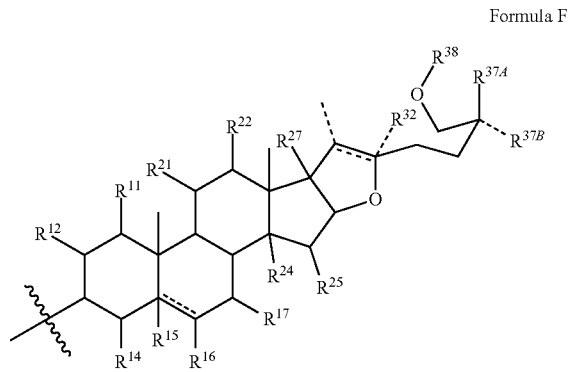

Formula F wherein
$R^{11}$, $R^{12}$, $R^{14}$, $R^{16}$, $R^{17}$, $R^{21}$, $R^{22}$, $R^{24}$, $R^{25}$ and $R^{27}$ are independently H, OH, =O, pharmacologically acceptable ester groups or pharmacologically acceptable ether groups;

$R^{15}$ is H when C-5, C-6 is a single bond, and nothing when C-5, C-6 is a double bond;
$R^{32}$ is either a hydroxyl or an alkoxyl group when C-20, C-22 is a single bond, or nothing when C-20, C-22 is a double bond;
$R^{37A}$ is H concurrently with $R^{37B}$ being $CH_3$, or $R^{37A}$ is $CH_3$ concurrently with $R^{37B}$ being H;
$R^{38}$ is H or a saccharide;

Formula G

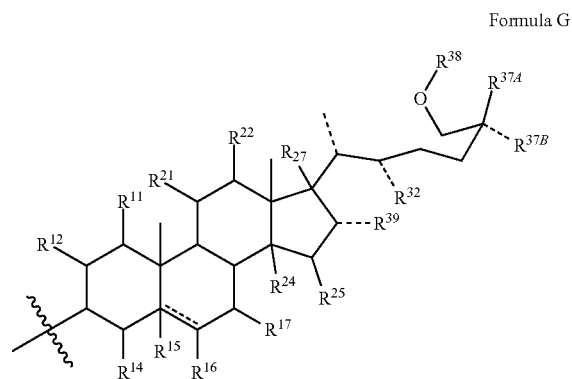

wherein
$R^{11}$, $R^{12}$, $R^{14}$, $R^{16}$, $R^{17}$, $R^{21}$, $R^{22}$, $R^{24}$, $R^{25}$ and $R^{27}$ are each independently H, OH, =O, pharmacologically acceptable ester groups or pharmacologically acceptable ether groups;
$R^{15}$ is H when C-5, C-6 is a single bond, and nothing when C-5, C-6 is a double bond;
$R^{32}$ and $R^{39}$ are each independently H, OH, =O, pharmacologically acceptable ester groups or pharmacologically acceptable ether groups;
$R^{37A}$ is H concurrently with $R^{37B}$ being $CH_3$, or $R^{37A}$ is $CH_3$ concurrently with $R^{37B}$ being H;
$R^{38}$ is H or a saccharide;
or a pharmaceutically acceptable salt thereof.

2. A compound according to claim 1 wherein the compound has the formula

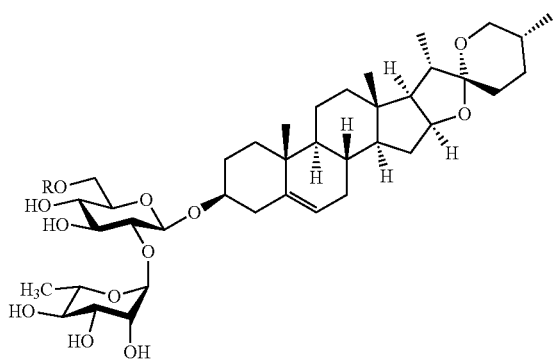

wherein R is as defined in claim 1;
or a pharmaceutically acceptable salt thereof.

3. A compound according to claim 2 wherein R is a moiety containing (1) at least one a hydrogen ion donor.

4. A compound according to claim 3 wherein the at least one hydrogen ion donor is selected from the group consisting of —$CO_2H$, —$SO_3H$ and —$PO_3H_2$.

5. A compound according to claim 3 wherein R is —$PO_3H_2$.

6. A compound according to claim 1 wherein R is a moiety containing at least one hydrogen ion acceptor.

7. A compound according to claim 6 wherein the hydrogen ion acceptor is —$NH_2$.

8. A compound according to claim 6 wherein R is $(CH_3)_2CHCH(NH_2)C(=O)$—.

9. A compound according to claim 1 wherein the compound is selected from the group consisting of:

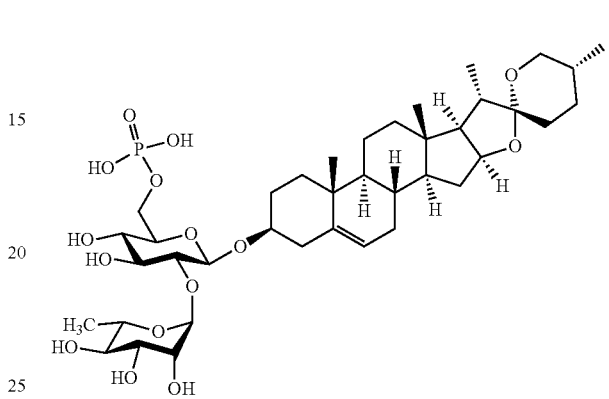

and

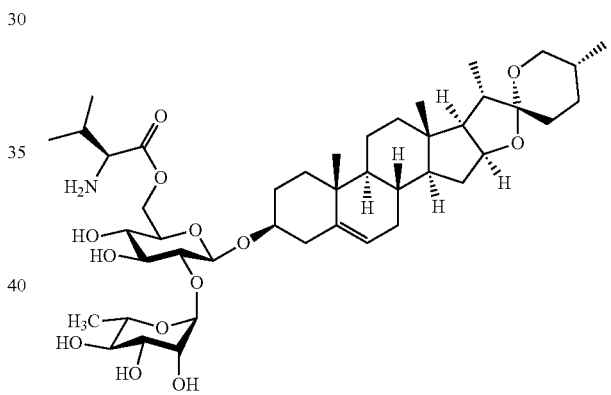

or a pharmaceutically acceptable salt thereof.

10. A compound according to claim 1 wherein the compound has the formula:

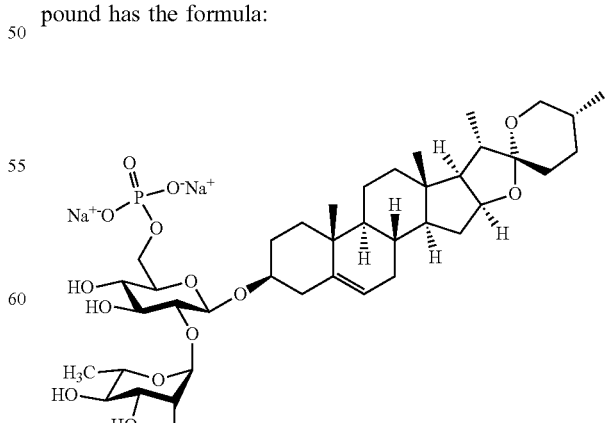

or wherein the compound has the formula:

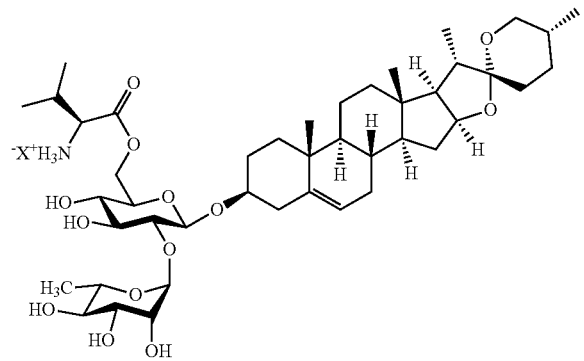

wherein X is $HO_2CCHCHCO_2-$.

11. A pharmaceutical composition containing a compound according to claim 1 or a pharmaceutically acceptable salt thereof and a pharmaceutically acceptable diluent, excipient or carrier.

12. A method of treatment of cancer in a subject the method comprising administration of a therapeutically effective amount of a compound according to claim 1 to a subject in need thereof.

13. A method according to claim 12 wherein the cancer is selected from the group consisting carcinoma, bladder cancer, bone cancer, brain tumours, breast cancer, cervical cancer, colorectal cancer including cancer of the colon, rectum, anus, and appendix, cancer of the oesophagus, Hodgkin's disease, kidney cancer, cancer of the larynx, leukaemia, liver cancer, lung cancer, lymphoma, melanoma, moles and dysplastic nevi, multiple myeloma, muscular cancer, non-Hodgkin's lymphoma, oral cancer, ovarian cancer, cancer of the pancreas, prostate cancer, sarcoma, skin cancer, stomach cancer, testicular cancer, teratoma, thyroid cancer, and cancer of the uterus.

14. A method according to claim 12 further comprising administration of a second anti-cancer agent.

15. A method according to claim 14 wherein the second anti-cancer agent is selected from one or more of a chemotherapeutic agent, an alkylating agent; an antimitotic agent; a topoisomerase inhibitor; a RNA/DNA antimetabolite; a DNA antimetabolite; a cellular process targeting agent; imatinib mesylate; trastuzumab; and gefitinib and anti (programmed cell death 1 receptor) PD-1 therapy; prembrozilab and nivomulab.

16. The method according to claim 15, wherein:
the alkylating agent is BCNU (carmustine), bisulfan, CCNU (lomustine), chlorambucil, cisplatin, melphan, mitomycin C, or thio-tepa;
the antimitotic agent is taxol (paclitaxel), docetaxel, vinblastine sulphate, or vincristine sulphate;
the topoisomerase inhibitor is doxorubicin, daunorubicin, m-AMSA (amsacrine), mitoxantrone, or VP-16 (etoposide);
the RNA/DNA antimetabolite is 5-fluorouracil or methotrexate; or
the DNA antimetabolite is Ara-C (cytarabine), hydroxyurea (hydroxycarbamide), or thioguanine (tioguanine).

17. A method of promoting the activity of an anti-cancer therapy in a subject the method comprising administration of an effective amount of a compound according to claim 1 to a subject in need thereof.

18. A method according to claim 17 wherein the anti-cancer therapy involves administration of one or more anti-cancer agents selected from the group consisting of a chemotherapeutic agent, an alkylating agent; an antimitotic agent; a topoisomerase inhibitor; a RNA/DNA antimetabolite; a DNA antimetabolite; a cellular process targeting agent; imatinib mesylate; trastuzumab; and gefitinib.

19. The method according to claim 18, wherein:
the alkylating agent is BCNU (carmustine), bisulfan, CCNU (lomustine), chlorambucil, cisplatin, melphan, mitomycin C, or thio-tepa;
the antimitotic agent is taxol (paclitaxel), docetaxel, vinblastine sulphate, or vincristine sulphate;
the topoisomerase inhibitor is doxorubicin, daunorubicin, m-AMSA (amsacrine), mitoxantrone, or VP-16 (etoposide);
the RNA/DNA antimetabolite is 5-fluorouracil or methotrexate; or
the DNA antimetabolite is Ara-C (cytarabine), hydroxyurea (hydroxycarbamide), or thioguanine (tioguanine).

20. A method of promoting an immune response in a subject, the method comprising administration of an effective amount of a compound according to claim 1 to a subject in need thereof.

21. A method of promoting an immune response to an agent in a subject, the method comprising administration of an effective amount of a compound according to claim 1 to a subject in need thereof.

22. A method according to claim 21 wherein the compound is administered simultaneously with the agent.

* * * * *